US012727881B2

(12) United States Patent
Euteneuer et al.

(10) Patent No.: US 12,727,881 B2
(45) Date of Patent: Sep. 8, 2026

(54) METHODS AND APPARATUS FOR DELIVERING STAPLES TO A TARGET TISSUE

(71) Applicant: Rotation Medical, Inc., Memphis, TN (US)

(72) Inventors: Charles L. Euteneuer, St. Michael, MN (US); Rebecca McCarville, Spring Park, MN (US); Duane Frion, Brooklyn Center, MN (US); Nathaniel Zenz-Olson, Blaine, MN (US); Diane M. Feehan, Corcoran, MN (US)

(73) Assignee: Rotation Medical, Inc.

( * ) Notice: Subject to any disclaimer, the term of this patent is extended or adjusted under 35 U.S.C. 154(b) by 152 days.

(21) Appl. No.: 18/368,276

(22) Filed: Sep. 14, 2023

(65) Prior Publication Data

US 2024/0000450 A1 Jan. 4, 2024

Related U.S. Application Data

(63) Continuation of application No. 16/747,205, filed on Jan. 20, 2020, now Pat. No. 11,793,510, which is a (Continued)

(51) Int. Cl.

*A61B 17/068* (2006.01)
*A61B 17/064* (2006.01)
(Continued)

(52) U.S. Cl.

CPC .......... *A61B 17/068* (2013.01); *A61B 17/064* (2013.01); *A61B 17/0642* (2013.01); (Continued)

(58) Field of Classification Search

CPC .............. A61B 17/068; A61B 17/0682; A61B 17/0642; A61B 2017/0645; A61B 17/064; A61B 17/0644; A61B 17/0643

See application file for complete search history.

(56) References Cited

U.S. PATENT DOCUMENTS 511,238 A 12/1893 Hieatzman
765,793 A 7/1904 Ruckel
(Continued)

FOREIGN PATENT DOCUMENTS

CA 2390508 A1 5/2001
EP 0142225 A1 5/1985
(Continued)

OTHER PUBLICATIONS

Bahler et al.; Trabecular Bypass Stents Decrease Intraocular Pressure in Cultured Human Anterior Segments; Am. J. Opthalmology; 138(6): 988-994; Dec. 2004.

(Continued)

*Primary Examiner* — Thomas McEvoy

(74) *Attorney, Agent, or Firm* — Seager, Tufte & Wickhem LLP

(57) ABSTRACT

A device for attaching a sheet-like implant to a target tissue includes a pilot member and a staple push rod. In some embodiments, the pilot member has a distal end and at least a pair of prongs extending from the distal end. The prongs are configured to form pilot holes when the distal end of the pilot member is pressed against the target tissue. The staple push rod is disposed within at least a portion of the pilot member and slidable relative thereto. The staple push rod includes at least a pair of stakes. Each stake is dimensioned to engage a surface of a staple to apply pushing forces thereto. Each stake is positioned relative to a prong along an inner surface of the pilot member so that the stakes advance into the pilot holes when the stakes are moved in a distal direction. Methods for attaching a sheet-like implant to a target tissue are also disclosed.

19 Claims, 16 Drawing Sheets

Related U.S. Application Data continuation of application No. 14/733,458, filed on Jun. 8, 2015, now Pat. No. 10,568,622, which is a continuation of application No. 13/889,687, filed on May 8, 2013, now Pat. No. 9,095,337, which is a continuation of application No. 12/794,551, filed on Jun. 4, 2010, now Pat. No. 8,821,536.

(60) Provisional application No. 61/313,051, filed on Mar. 11, 2010, provisional application No. 61/253,800, filed on Oct. 21, 2009, provisional application No. 61/184,198, filed on Jun. 4, 2009.

(51) Int. Cl.
*A61F 2/00* (2006.01)
*A61F 2/08* (2006.01)
*A61F 2/30* (2006.01)
*A61B 17/00* (2006.01)
*A61B 17/04* (2006.01)

(52) U.S. Cl.
CPC ...... *A61B 17/0644* (2013.01); *A61B 17/0682* (2013.01); *A61F 2/0063* (2013.01); *A61F 2/08* (2013.01); *A61F 2/30749* (2013.01); *A61B 2017/00004* (2013.01); *A61B 2017/0046* (2013.01); *A61B 2017/00862* (2013.01); *A61B 17/0491* (2013.01); *A61B 17/0643* (2013.01); *A61B 2017/0645* (2013.01); *A61F 2220/0016* (2013.01)

(56) References Cited

U.S. PATENT DOCUMENTS 1,728,316 A 9/1929 Wachenfeldt
1,855,546 A 4/1932 File
1,868,100 A 7/1932 Goodstein
1,910,688 A 5/1933 Goodstein
1,940,351 A 12/1933 Howard
2,034,785 A 3/1936 Wappler
2,075,508 A 3/1937 Davidson
2,131,321 A 9/1938 Hart
2,158,242 A 5/1939 Maynard
2,199,025 A 4/1940 Conn
2,201,610 A 5/1940 Dawson, Jr.
2,254,620 A 9/1941 Miller
2,277,931 A 3/1942 Moe
2,283,814 A 5/1942 La Place
2,316,297 A 4/1943 Southerland et al.
2,421,193 A 5/1947 Gardner
2,571,813 A 10/1951 Austin
2,630,316 A 3/1953 Foster
2,684,070 A 7/1954 Kelsey
2,744,251 A 5/1956 Vollmer
2,790,341 A 4/1957 Keep et al.
2,817,339 A 12/1957 Sullivan
2,825,162 A 3/1958 Flood
2,881,762 A 4/1959 Lowrie
2,910,067 A 10/1959 White
3,068,870 A 12/1962 Levin
3,077,812 A 2/1963 Dietrich
3,103,666 A 9/1963 Bone
3,123,077 A 3/1964 Alcamo
3,209,754 A 10/1965 Brown
3,221,746 A 12/1965 Noble
3,470,834 A 10/1969 Bone
3,527,223 A 9/1970 Shein
3,570,497 A 3/1971 Lemole
3,577,837 A 5/1971 Bader, Jr.
3,579,831 A 5/1971 Stevens et al.
3,643,851 A 2/1972 Green et al.
3,687,138 A 8/1972 Jarvik
3,716,058 A 2/1973 Tanner, Jr.
3,717,294 A 2/1973 Green
3,757,629 A 9/1973 Schneider
3,777,538 A 12/1973 Weatherly et al.
3,837,555 A 9/1974 Green
3,845,772 A 11/1974 Smith
3,875,648 A 4/1975 Bone
3,960,147 A 6/1976 Murray
3,976,079 A 8/1976 Samuels et al.
4,014,492 A 3/1977 Rothfuss
4,127,227 A 11/1978 Green
4,259,959 A 4/1981 Walker
4,263,903 A 4/1981 Griggs
4,265,226 A 5/1981 Cassimally
4,317,451 A 3/1982 Cerwin et al.
4,400,833 A 8/1983 Kurland
4,422,567 A 12/1983 Haynes
4,454,875 A 6/1984 Pratt et al.
4,480,641 A 11/1984 Failla et al.
4,485,816 A 12/1984 Krumme
4,526,174 A 7/1985 Froehlich
4,549,545 A 10/1985 Levy
4,570,623 A 2/1986 Ellison et al.
4,595,007 A 6/1986 Mericle
4,624,254 A 11/1986 McGarry et al.
4,627,437 A 12/1986 Bedi et al.
4,632,100 A 12/1986 Somers et al.
4,635,637 A 1/1987 Schreiber
4,669,473 A 6/1987 Richards et al.
4,696,300 A 9/1987 Anderson
4,719,917 A 1/1988 Barrows et al.
4,738,255 A 4/1988 Goble et al.
4,741,330 A 5/1988 Hayhurst
4,762,260 A 8/1988 Richards et al.
4,799,495 A 1/1989 Hawkins et al.
4,809,695 A 3/1989 Gwathmey et al.
4,821,721 A 4/1989 Chin et al.
4,851,005 A 7/1989 Hunt et al.
4,858,608 A 8/1989 McQuilkin
4,884,572 A 12/1989 Bays et al.
4,887,601 A 12/1989 Richards
4,924,866 A 5/1990 Yoon
4,930,674 A 6/1990 Barak
4,968,315 A 11/1990 Gatturna
4,976,715 A 12/1990 Bays et al.
4,994,073 A 2/1991 Green
4,997,436 A 3/1991 Oberlander
5,002,563 A 3/1991 Pyka et al.
5,013,316 A 5/1991 Goble et al.
5,015,249 A 5/1991 Nakao et al.
5,037,422 A 8/1991 Hayhurst et al.
5,041,129 A 8/1991 Hayhurst et al.
5,046,513 A 9/1991 Gatturna et al.
5,053,047 A 10/1991 Yoon
5,059,206 A 10/1991 Winters
5,062,563 A 11/1991 Green et al.
5,100,417 A 3/1992 Cerier et al.
5,102,421 A 4/1992 Anspach, Jr.
5,116,357 A 5/1992 Eberbach
5,122,155 A 6/1992 Eberbach
5,123,913 A 6/1992 Wilk et al.
RE34,021 E 8/1992 Mueller et al.
5,141,515 A 8/1992 Eberbach
5,141,520 A 8/1992 Goble et al.
5,156,609 A 10/1992 Nakao et al.
5,156,616 A 10/1992 Meadows et al.
5,167,665 A 12/1992 McKinney
5,171,259 A 12/1992 Inoue
5,174,295 A 12/1992 Christian et al.
5,174,487 A 12/1992 Rothfuss et al.
5,176,682 A 1/1993 Chow
5,176,692 A 1/1993 Wilk et al.
5,203,787 A 4/1993 Noblitt et al.
5,217,472 A 6/1993 Green et al.
5,222,961 A 6/1993 Nakao et al.
5,224,946 A 7/1993 Hayhurst et al.
5,242,457 A 9/1993 Akopov et al.
5,246,441 A 9/1993 Ross et al.
5,251,642 A 10/1993 Handlos
5,261,914 A 11/1993 Warren
5,269,753 A 12/1993 Wilk

(56) References Cited

U.S. PATENT DOCUMENTS 5,269,783 A 12/1993 Sander
5,282,829 A 2/1994 Hermes
5,289,963 A 3/1994 McGarry et al.
5,290,217 A 3/1994 Campos
5,304,187 A 4/1994 Green et al.
5,333,624 A 8/1994 Tovey
5,342,396 A 8/1994 Cook
5,350,400 A 9/1994 Esposito et al.
5,352,229 A 10/1994 Goble et al.
5,354,292 A 10/1994 Braeuer et al.
5,364,408 A 11/1994 Gordon
5,366,460 A 11/1994 Eberbach
5,370,650 A 12/1994 Tovey et al.
5,372,604 A 12/1994 Trott
5,380,334 A 1/1995 Torrie et al.
5,383,477 A 1/1995 DeMatteis
5,397,332 A 3/1995 Kammerer et al.
5,403,326 A 4/1995 Harrison et al.
5,405,360 A 4/1995 Tovey
5,411,522 A 5/1995 Trott
5,411,523 A 5/1995 Goble
5,417,691 A 5/1995 Hayhurst
5,417,712 A 5/1995 Whittaker et al.
5,425,490 A 6/1995 Goble et al.
5,441,502 A 8/1995 Bartlett
5,441,508 A 8/1995 Gazielly et al.
5,456,720 A 10/1995 Schultz et al.
5,464,403 A 11/1995 Kieturakis et al.
5,478,354 A 12/1995 Tovey et al.
5,486,197 A 1/1996 Le et al.
5,497,933 A 3/1996 DeFonzo et al.
5,500,000 A 3/1996 Feagin et al.
5,501,695 A 3/1996 Anspach, Jr. et al.
5,503,623 A 4/1996 Tilton, Jr.
5,505,735 A 4/1996 Li
5,507,754 A 4/1996 Green et al.
5,520,700 A 5/1996 Beyar et al.
5,522,817 A 6/1996 Sander et al.
5,545,180 A 8/1996 Le et al.
5,560,532 A 10/1996 DeFonzo et al.
5,562,689 A 10/1996 Green et al.
5,569,306 A 10/1996 Thal et al.
5,582,616 A 12/1996 Bolduc et al.
5,584,835 A 12/1996 Greenfield
5,618,314 A 4/1997 Harwin et al.
5,622,257 A 4/1997 Deschenes et al.
5,628,751 A 5/1997 Sander et al.
5,643,319 A 7/1997 Green et al.
5,643,321 A 7/1997 McDevitt
5,647,874 A 7/1997 Hayhurst
5,649,963 A 7/1997 McDevitt
5,662,683 A 9/1997 Kay
5,667,513 A 9/1997 Torrie et al.
5,674,245 A 10/1997 Ilgen
5,681,342 A 10/1997 Benchetrit
5,702,215 A 12/1997 Li
5,713,903 A 2/1998 Sander et al.
5,720,753 A 2/1998 Sander et al.
5,725,541 A 3/1998 Anspach, III et al.
5,741,282 A 4/1998 Anspach, III et al.
5,766,246 A 6/1998 Mulhauser et al.
5,782,864 A 7/1998 Lizardi
5,797,909 A 8/1998 Michelson
5,797,931 A 8/1998 Bito et al.
5,797,963 A 8/1998 McDevitt
5,807,403 A 9/1998 Beyar et al.
5,830,221 A 11/1998 Stein et al.
5,836,961 A 11/1998 Kieturakis et al.
5,868,762 A 2/1999 Cragg et al.
5,873,891 A 2/1999 Sohn
5,885,258 A 3/1999 Sachdeva et al.
5,885,294 A 3/1999 Pedlick et al.
5,893,856 A 4/1999 Jacob et al.
5,904,696 A 5/1999 Rosenman
5,919,184 A 7/1999 Tilton, Jr.
5,922,026 A 7/1999 Chin
5,928,244 A 7/1999 Tovey et al.
5,948,000 A 9/1999 Larsen et al.
5,957,939 A 9/1999 Heaven et al.
5,957,953 A 9/1999 Dipoto et al.
5,968,044 A 10/1999 Nicholson et al.
5,980,557 A 11/1999 Iserin et al.
5,988,171 A 11/1999 Sohn et al.
5,989,265 A 11/1999 Bouquet De La Joliniere et al.
5,997,552 A 12/1999 Person et al.
6,063,088 A 5/2000 Winslow
6,156,045 A 12/2000 Ulbrich et al.
6,179,840 B1 1/2001 Bowman
6,193,731 B1 2/2001 Oppelt et al.
6,193,733 B1 2/2001 Adams
6,245,072 B1 6/2001 Zdeblick et al.
6,302,885 B1 10/2001 Essiger
6,312,442 B1 11/2001 Kieturakis et al.
6,315,789 B1 11/2001 Cragg
6,318,616 B1 11/2001 Pasqualucci et al.
6,322,563 B1 11/2001 Cummings et al.
6,325,805 B1 12/2001 Ogilvie et al.
6,387,113 B1 5/2002 Hawkins et al.
6,391,333 B1 5/2002 Li et al.
6,413,274 B1 7/2002 Pedros
6,425,900 B1 7/2002 Knodel et al.
6,436,110 B2 8/2002 Bowman et al.
6,447,522 B2 9/2002 Gambale et al.
6,447,524 B1 9/2002 Knodel et al.
6,478,803 B1 11/2002 Kapec et al.
6,482,178 B1 11/2002 Andrews et al.
6,482,210 B1 11/2002 Skiba et al.
6,506,190 B1 1/2003 Walshe
6,511,499 B2 1/2003 Schmieding et al.
6,517,564 B1 2/2003 Grafton et al.
6,524,316 B1 2/2003 Nicholson et al.
6,527,795 B1 3/2003 Lizardi
6,530,933 B1 3/2003 Yeung et al.
6,540,769 B1 4/2003 Miller, III
6,551,333 B2 4/2003 Kuhns et al.
6,554,852 B1 4/2003 Oberlander
6,569,186 B1 5/2003 Winters et al.
6,575,976 B2 6/2003 Grafton
6,599,289 B1 7/2003 Bojarski et al.
6,620,185 B1 9/2003 Harvie et al.
6,629,988 B2 10/2003 Weadock
6,638,297 B1 10/2003 Huitema
6,648,893 B2 11/2003 Dudasik
6,666,872 B2 12/2003 Barreiro et al.
6,673,094 B1 1/2004 McDevitt et al.
6,685,728 B2 2/2004 Sinnott et al.
6,692,506 B1 2/2004 Ory et al.
6,723,099 B1 4/2004 Goshert
6,726,704 B1 4/2004 Loshakove et al.
6,726,705 B2 4/2004 Peterson et al.
6,740,100 B2 5/2004 Demopulos et al.
6,746,472 B2 6/2004 Frazier et al.
6,764,500 B1 7/2004 Muijs Van De Moer et al.
6,770,073 B2 8/2004 McDevitt et al.
6,779,701 B2 8/2004 Bailly et al.
6,800,081 B2 10/2004 Parodi
6,835,206 B2 12/2004 Jackson
6,849,078 B2 2/2005 Durgin et al.
6,887,259 B2 5/2005 Lizardi
6,926,723 B1 8/2005 Mulhauser et al.
6,932,834 B2 8/2005 Lizardi et al.
6,939,365 B1 9/2005 Fogarty et al.
6,946,003 B1 9/2005 Wolowacz et al.
6,949,117 B2 9/2005 Gambale et al.
6,964,685 B2 11/2005 Murray et al.
6,966,916 B2 11/2005 Kumar
6,972,027 B2 12/2005 Fallin et al.
6,984,241 B2 1/2006 Lubbers et al.
6,991,597 B2 1/2006 Gellman et al.
7,008,435 B2 3/2006 Cummins
7,021,316 B2 4/2006 Leiboff
7,025,772 B2 4/2006 Gellman et al.
7,033,379 B2 4/2006 Peterson
7,037,324 B2 5/2006 Martinek

(56) References Cited

U.S. PATENT DOCUMENTS 7,048,171 B2 5/2006 Thornton et al.
7,063,711 B1 6/2006 Loshakove et al.
7,083,638 B2 8/2006 Foerster
7,087,064 B1 8/2006 Hyde
7,112,214 B2 9/2006 Peterson et al.
7,118,581 B2 10/2006 Fridén
7,144,413 B2 12/2006 Wilford et al.
7,144,414 B2 12/2006 Harvie et al.
7,150,750 B2 12/2006 Damarati
7,153,314 B2 12/2006 Laufer et al.
7,160,314 B2 1/2007 Sgro et al.
7,160,326 B2 1/2007 Ball
7,163,551 B2 1/2007 Anthony et al.
7,163,563 B2 1/2007 Schwartz et al.
7,169,157 B2 1/2007 Kayan
7,189,251 B2 3/2007 Kay
7,201,754 B2 4/2007 Stewart et al.
7,214,232 B2 5/2007 Bowman et al.
7,226,469 B2 6/2007 Benavitz et al.
7,229,452 B2 6/2007 Kayan
7,247,164 B1 7/2007 Ritchart et al.
7,303,577 B1 12/2007 Dean
7,309,337 B2 12/2007 Colleran et al.
7,320,692 B1 1/2008 Bender et al.
7,320,701 B2 1/2008 Haut et al.
7,322,935 B2 1/2008 Palmer et al.
7,326,231 B2 2/2008 Phillips et al.
7,343,920 B2 3/2008 Toby et al.
7,368,124 B2 5/2008 Chun et al.
7,377,934 B2 5/2008 Lin et al.
7,381,213 B2 6/2008 Lizardi
7,390,329 B2 6/2008 Westra et al.
7,399,304 B2 7/2008 Gambale et al.
7,404,824 B1 7/2008 Webler et al.
7,416,554 B2 8/2008 Lam et al.
7,452,368 B2 11/2008 Liberatore et al.
7,460,913 B2 12/2008 Kuzma et al.
7,463,933 B2 12/2008 Wahlstrom et al.
7,465,308 B2 12/2008 Sikora et al.
7,481,832 B1 1/2009 Meridew et al.
7,485,124 B2 2/2009 Kuhns et al.
7,497,854 B2 3/2009 Gill et al.
7,500,972 B2 3/2009 Voegele et al.
7,500,980 B2 3/2009 Gill et al.
7,500,983 B1 3/2009 Kaiser et al.
7,503,474 B2 3/2009 Hillstead et al.
7,506,791 B2 3/2009 Omaits et al.
7,559,941 B2 7/2009 Zannis et al.
7,572,276 B2 8/2009 Lim et al.
7,585,311 B2 9/2009 Green et al.
7,766,208 B2 8/2010 Epperly et al.
7,771,440 B2 8/2010 Ortiz et al.
7,776,057 B2 8/2010 Laufer et al.
7,780,685 B2 8/2010 Hunt et al.
7,785,255 B2 8/2010 Malkani
7,807,192 B2 10/2010 Li et al.
7,819,880 B2 10/2010 Zannis et al.
7,918,879 B2 4/2011 Yeung et al.
8,114,101 B2 2/2012 Criscuolo et al.
8,197,837 B2 6/2012 Jamiolkowski et al.
8,668,718 B2 3/2014 Euteneuer et al.
8,763,878 B2 7/2014 Euteneuer et al.
8,821,536 B2 9/2014 Euteneuer et al.
8,821,537 B2 9/2014 Euteneuer et al.
8,864,780 B2 10/2014 Euteneuer et al.
9,033,201 B2 5/2015 Euteneuer
9,101,460 B2 8/2015 Euteneuer et al.
9,107,661 B2 8/2015 Euteneuer et al.
9,113,977 B2 8/2015 Euteneuer et al.
9,125,650 B2 9/2015 Euteneuer et al.
9,179,961 B2 11/2015 Euteneuer et al.
9,198,751 B2 12/2015 Euteneuer et al.
9,204,940 B2 12/2015 Euteneuer et al.
9,247,978 B2 2/2016 Euteneuer et al.
9,271,726 B2 3/2016 Euteneuer
9,314,314 B2 4/2016 Euteneuer et al.
9,314,331 B2 4/2016 Euteneuer et al.
9,370,356 B2 6/2016 Euteneuer et al.
9,393,103 B2 7/2016 Van Kampen et al.
9,566,063 B2 2/2017 Euteneuer et al.
2002/0077687 A1 6/2002 Ahn
2002/0090725 A1 7/2002 Simpson et al.
2002/0123767 A1 9/2002 Prestel
2002/0165559 A1 11/2002 Grant et al.
2003/0073979 A1 4/2003 Naimark et al.
2003/0125748 A1 7/2003 Li et al.
2003/0212456 A1 11/2003 Lipchitz et al.
2004/0059416 A1 3/2004 Murray et al.
2004/0138705 A1 7/2004 Heino et al.
2004/0167519 A1 8/2004 Weiner et al.
2005/0015021 A1 1/2005 Shiber
2005/0049618 A1 3/2005 Masuda et al.
2005/0051597 A1 3/2005 Toledano
2005/0059996 A1 3/2005 Bauman et al.
2005/0060033 A1 3/2005 Vacanti et al.
2005/0107807 A1 5/2005 Nakao
2005/0113736 A1 5/2005 Orr et al.
2005/0171569 A1 8/2005 Girard et al.
2005/0187576 A1 8/2005 Whitman et al.
2005/0240222 A1 10/2005 Shipp
2005/0274768 A1 12/2005 Cummins et al.
2006/0074423 A1 4/2006 Alleyne et al.
2006/0178743 A1 8/2006 Carter
2006/0235442 A1 10/2006 Huitema
2006/0293760 A1 12/2006 Dedeyne
2007/0078477 A1 4/2007 Heneveld, Sr. et al.
2007/0083236 A1 4/2007 Sikora et al.
2007/0112361 A1 5/2007 Schonholz et al.
2007/0179531 A1 8/2007 Thornes
2007/0185506 A1 8/2007 Jackson
2007/0190108 A1 8/2007 Datta et al.
2007/0219558 A1 9/2007 Deutsch
2007/0270804 A1 11/2007 Chudik
2007/0288023 A1 12/2007 Pellegrino et al.
2008/0027470 A1 1/2008 Hart et al.
2008/0051888 A1 2/2008 Ratcliffe et al.
2008/0065153 A1 3/2008 Allard et al.
2008/0090936 A1 4/2008 Fujimura et al.
2008/0125869 A1 5/2008 Paz et al.
2008/0135600 A1 6/2008 Hiranuma et al.
2008/0173691 A1 7/2008 Mas et al.
2008/0188874 A1 8/2008 Henderson
2008/0188936 A1 8/2008 Ball et al.
2008/0195119 A1 8/2008 Ferree
2008/0200949 A1 8/2008 Hiles et al.
2008/0241213 A1 10/2008 Chun et al.
2008/0272173 A1 11/2008 Coleman et al.
2008/0306408 A1 12/2008 Lo
2009/0001122 A1 1/2009 Prommersberger et al.
2009/0012521 A1 1/2009 Axelson, Jr. et al.
2009/0030434 A1 1/2009 Paz et al.
2009/0069806 A1 3/2009 De La Mora Levy et al.
2009/0076541 A1 3/2009 Chin et al.
2009/0105535 A1 4/2009 Green et al.
2009/0112085 A1 4/2009 Eby
2009/0134198 A1 5/2009 Knodel et al.
2009/0156986 A1 6/2009 Trenhaile
2009/0156997 A1 6/2009 Trenhaile
2009/0182245 A1 7/2009 Zambelli
2009/0242609 A1 10/2009 Kanner
2010/0145367 A1 6/2010 Ratcliffe
2010/0147922 A1 6/2010 Olson
2010/0163598 A1 7/2010 Belzer
2010/0191332 A1 7/2010 Euteneuer et al.
2010/0241227 A1 9/2010 Euteneuer et al.
2010/0249801 A1 9/2010 Sengun et al.
2010/0256675 A1 10/2010 Romans
2010/0274278 A1 10/2010 Fleenor et al.
2010/0292715 A1 11/2010 Nering et al.
2010/0292791 A1 11/2010 Lu et al.
2010/0312250 A1 12/2010 Euteneuer et al.
2010/0312275 A1 12/2010 Euteneuer et al.
2010/0327042 A1 12/2010 Amid et al.
2011/0000950 A1 1/2011 Euteneuer et al.

(56) References Cited

U.S. PATENT DOCUMENTS

| | | | |
|---|---|---|---|
| 2011/0004221 | A1 | 1/2011 | Euteneuer et al. |
| 2011/0011917 | A1 | 1/2011 | Loulmet |
| 2011/0034942 | A1 | 2/2011 | Levin et al. |
| 2011/0040310 | A1 | 2/2011 | Levin et al. |
| 2011/0040311 | A1 | 2/2011 | Levin et al. |
| 2011/0066166 | A1 | 3/2011 | Levin et al. |
| 2011/0106154 | A1 | 5/2011 | DiMatteo et al. |
| 2011/0114700 | A1 | 5/2011 | Baxter, III et al. |
| 2011/0224702 | A1 | 9/2011 | Van Kampen et al. |
| 2011/0264149 | A1 | 10/2011 | Pappalardo et al. |
| 2012/0160893 | A1 | 6/2012 | Harris et al. |
| 2012/0193391 | A1 | 8/2012 | Michler et al. |
| 2012/0209401 | A1 | 8/2012 | Euteneuer et al. |
| 2012/0211543 | A1 | 8/2012 | Euteneuer |
| 2012/0248171 | A1 | 10/2012 | Bailly et al. |
| 2012/0316608 | A1 | 12/2012 | Foley |
| 2013/0153627 | A1 | 6/2013 | Euteneuer et al. |
| 2013/0153628 | A1 | 6/2013 | Euteneuer |
| 2013/0158554 | A1 | 6/2013 | Euteneuer et al. |
| 2013/0158587 | A1 | 6/2013 | Euteneuer et al. |
| 2013/0158661 | A1 | 6/2013 | Euteneuer et al. |
| 2013/0172920 | A1 | 7/2013 | Euteneuer et al. |
| 2013/0172997 | A1 | 7/2013 | Euteneuer et al. |
| 2013/0184716 | A1 | 7/2013 | Euteneuer et al. |
| 2013/0240598 | A1 | 9/2013 | Euteneuer et al. |
| 2013/0245627 | A1 | 9/2013 | Euteneuer et al. |
| 2013/0245682 | A1 | 9/2013 | Euteneuer et al. |
| 2013/0245706 | A1 | 9/2013 | Euteneuer et al. |
| 2013/0245707 | A1 | 9/2013 | Euteneuer et al. |
| 2013/0245762 | A1 | 9/2013 | Van Kampen et al. |
| 2013/0245774 | A1 | 9/2013 | Euteneuer et al. |

FOREIGN PATENT DOCUMENTS

| | | | |
|---|---|---|---|
| EP | 0298400 | A1 | 1/1989 |
| EP | 0390613 | A1 | 10/1990 |
| EP | 0543499 | A1 | 5/1993 |
| EP | 0548998 | A1 | 6/1993 |
| EP | 0557963 | A1 | 9/1993 |
| EP | 0589306 | A2 | 3/1994 |
| EP | 0908152 | A1 | 4/1999 |
| EP | 1491157 | A1 | 12/2004 |
| EP | 1559379 | A1 | 8/2005 |
| EP | 2030576 | A2 | 3/2009 |
| GB | 2154688 | A | 9/1985 |
| GB | 2397240 | A | 7/2004 |
| JP | 58188442 | A | 11/1983 |
| JP | 22005506122 | A | 3/2005 |
| JP | 2006515774 | A | 6/2006 |
| WO | 8505025 | A1 | 11/1985 |
| WO | 0176456 | A2 | 10/2001 |
| WO | 0234140 | A2 | 5/2002 |
| WO | 03105670 | A2 | 12/2003 |
| WO | 2004000138 | A1 | 12/2003 |
| WO | 2004093690 | A1 | 11/2004 |
| WO | 2005016389 | A2 | 2/2005 |
| WO | 2006086679 | A1 | 8/2006 |
| WO | 2007014910 | A1 | 2/2007 |
| WO | 2007030676 | A2 | 3/2007 |
| WO | 2007078978 | A2 | 7/2007 |
| WO | 2007082088 | A2 | 7/2007 |
| WO | 2008111073 | A2 | 9/2008 |
| WO | 2008111078 | A2 | 9/2008 |
| WO | 2008139473 | A2 | 11/2008 |
| WO | 2009079211 | A1 | 6/2009 |
| WO | 2009143331 | A1 | 11/2009 |
| WO | 2011095890 | A2 | 8/2011 |
| WO | 2011128903 | A2 | 10/2011 |

OTHER PUBLICATIONS

Chamay et al.; Digital Contracture Deformity After Implantation of a Silicone Prosthesis: Light and Electron Microscopic Study; The Journal of Hand Surgery; 3(3): 266-270; May 1978.

D'Ermo et al.; Our Results with the Operation of ab externo; Ophthalmologica; 168: 347-355; 1971.

France et al.; Biomechanical Evaluation of Rotator Cuff Fixation Methods; The American Journal of Sports Medicine; 17(2): 176-181; Mar.-Apr. 1989.

Goodship et al.; An Assessment of Filamentous Carbon Fibre for the Treatment of Tendon Injury in the Horse; Veterinary Record; 106: 217-221; Mar. 8, 1980.

Hunter et al.; Flexor-Tendon Reconstruction in Severely Damaged Hands; The Journal of Bone and Joint Surgery (American Volume); 53-A(5): 329-358; Jul. 1971.

Johnstone et al.; Microsurgery of Schlemm's Canal and the Human Aqueous Outflow System; Am. J. Opthalmology; 76(6): 906-917; Dec. 1973.

Kowalsky et al.; Evaluation of Suture Abrasion Against Rotator Cuff Tendon and Proximal Humerus Bone; Arthroscopy: The Journal of Arthroscopic and Related Surgery; 24(3): 329-334; Mar. 2008.

Lee et al.; Aqueous-Venous and Intraocular Pressure; Preliminary Report of Animal Studies; Investigative Ophthalmology; 5(1):59-64; Feb. 1966.

Maepea et al.; The Pressures in the Episcleral Veins, Schlemm's Canal and the Trabecular Meshwork in Monkeys: Effects of Changes in Intraocular Pressure; Exp. Eye Res.; 49: 645-663; Oct. 1989.

Nicolle et al.; A Silastic Tendon Prosthesis as an Adjunct to Flexor Tendon Grafting: An Experimental and Clinical Evaluation; British Journal of Plastic Surgery; 22(3-4): 224-236; 1969.

Rubin et al.; The Use of Acellular Biologic Tissue Patches in Foot and Ankle Surgery; Clinics in Podiatric Medicine and Surgery; 22: 533-552; Oct. 2005.

Schultz; Canaloplasty Procedure Shows Promise for Open-Angle Glaucoma in European Study; Ocular Surgery News; pp. 34-35; Mar. 1, 2007.

Spiegel et al.; Schlemm's Canal Implant: A New Method to Lower Intraocular Pressure in Patients with POAG; Ophthalmic Surgery and Lasers; 30(6): 492-494; Jun. 1999.

Stetson et al.; Arthroscopic Treatment of Partial Rotator Cuff Tears; Operative Techniques in Sports Medicine; 12(2): 135-148; Apr. 2004.

Valdez et al.; Repair of Digital Flexor Tendon Lacerations in the Horse, Using Carbon Fiber Implants; JAYMA; 177(5): 427-435; Sep. 1, 1980.

Wikipedia, The Free Encyclopedia; Rotator Cuff Tear; Downloaded from: <http://en.wikipedia.org/Rotator_cuff_tear> on Dec. 6, 2012; 14 pages.

Alexander et al.; Ligament and Tendon Repair with an Absorbable Polymer-Coated Carbon Fiber Stent; Bulletin of the Hospital for Joint Diseases Orthopaedic Institute; 46(2): 155-173; Fall 1986.

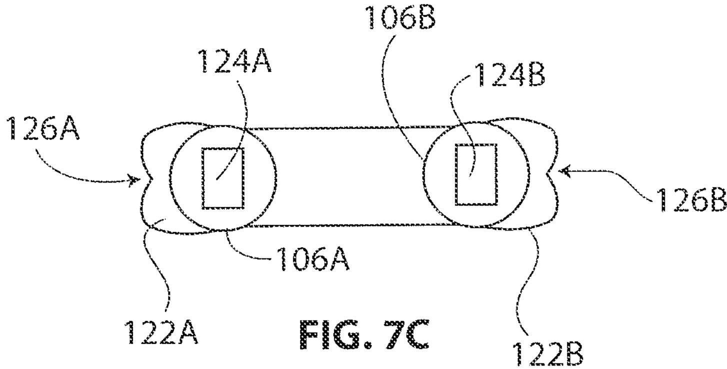
FIG. 7C
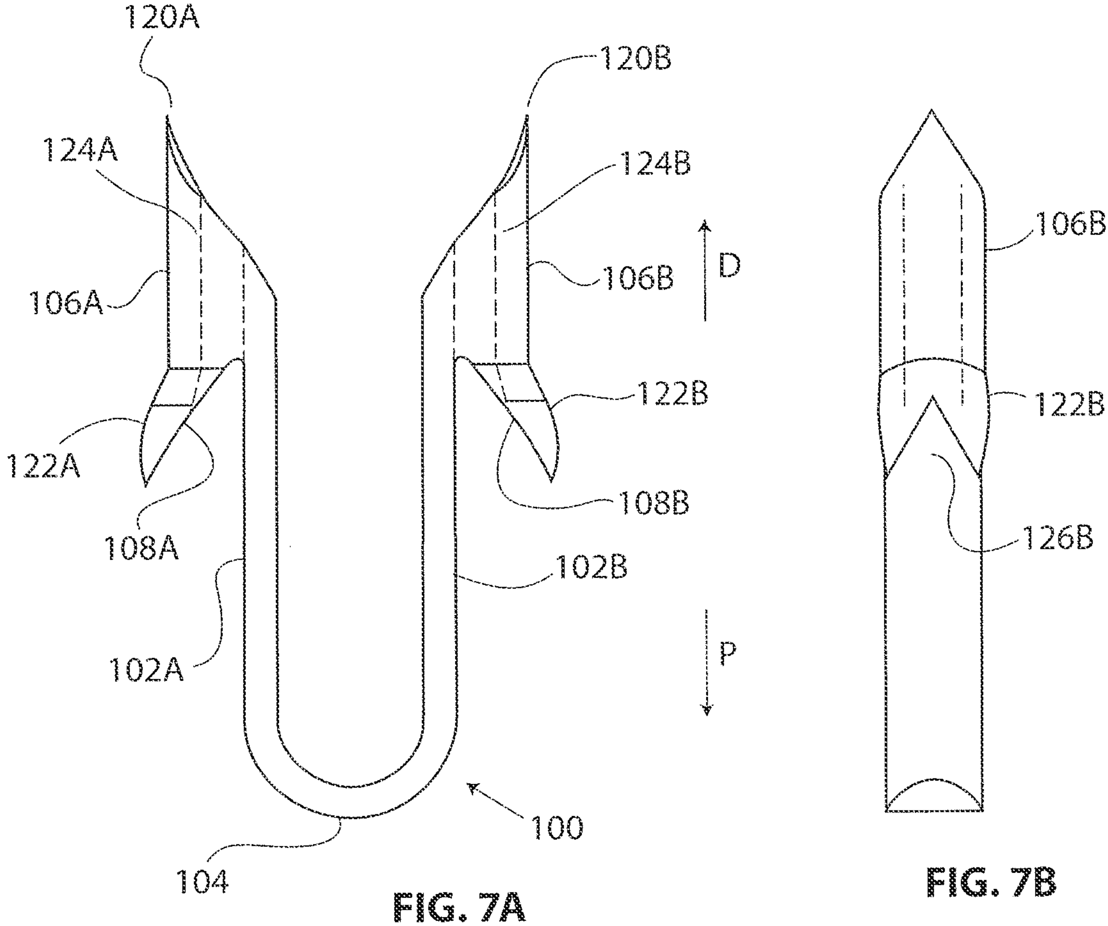
FIG. 7A
FIG. 7B 154B
154A

146

D
158
154A
154B
LA
DA
168
166
146

170
D
LB
146

152
150

METHODS AND APPARATUS FOR DELIVERING STAPLES TO A TARGET TISSUE

CROSS REFERENCE TO RELATED APPLICATIONS

This application is a continuation of U.S. application Ser. No. 16/747,205, filed Jan. 20, 2020, which is a continuation of U.S. application Ser. No. 14/733,458, filed Jun. 8, 2015, which is a continuation of U.S. application Ser. No. 13/889,687, filed May 8, 2013, which is a continuation of U.S. application Ser. No. 12/794,551, filed Jun. 4, 2010, which claims the benefit of U.S. provisional application Ser. No. 61/313,051 filed Mar. 11, 2010; U.S. provisional application Ser. No. 61/253,800, filed Oct. 21, 2009; and U.S. provisional application Ser. No. 61/184,198, filed Jun. 4, 2009, the disclosures of each incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to orthopedic medicine and surgery. More particularly, the present invention relates to methods and apparatus for delivery and fixation of sheet-like materials, such as for treating articulating joints.

BACKGROUND OF THE INVENTION

The glenohumeral joint of the shoulder is found where the head of the humerus mates with a shallow depression in the scapula. This shallow depression is known as the glenoid fossa. Six muscles extend between the humerus and scapula and actuate the glenohumeral joint. These six muscles include the deltoid, the *teres* major, and the four rotator cuff muscles. As disclosed by Ball et al. in U.S. Patent Publication No. US 2008/0188936 A1 and as illustrated in FIG. 1 the rotator cuff muscles are a complex of four muscles. These four muscles are the supraspinatus, the infraspinatus, the subscapularis, and the *teres* minor. The centering and stabilizing roles played by the rotator cuff muscles are critical to the proper function of the shoulder. The rotator cuff muscles provide a wide variety of moments to rotate the humerus and to oppose unwanted components of the deltoid and pectoralis muscle forces.

The four muscles of the rotator cuff arise from the scapula 12. The distal tendons of the rotator cuff muscles splay out and interdigitate to form a common continuous insertion on the humerus 14. The subscapularis 16 arises from the anterior aspect of the scapula 12 and attaches over much of the lesser tuberosity of the humerous. The supraspinatus muscle 18 arises from the supraspinatus fossa of the posterior scapula, passes beneath the acromion and the acromioclavicular joint, and attaches to the superior aspect of the greater tuberosity 11. The infraspinatus muscle 13 arises from the infraspinous fossa of the posterior scapula and attaches to the posterolateral aspect of the greater tuberosity 11. The *teres* minor 15 arises from the lower lateral aspect of the scapula 12 and attaches to the lower aspect of the greater tuberosity 11.

The mechanics of the rotator cuff muscles 10 are complex. The rotator cuff muscles 10 rotate the humerus 14 with respect to the scapula 12, compress the humeral head 17 into the glenoid fossa providing a critical stabilizing mechanism to the shoulder (known as concavity compression), and provide muscular balance. The supraspinatus and infraspinatus provide 45 percent of abduction and 90 percent of external rotation strength. The supraspinatus and deltoid muscles are equally responsible for producing torque about the shoulder joint in the functional planes of motion.

The rotator cuff muscles 10 are critical elements of this shoulder muscle balance equation. The human shoulder has no fixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action. Injury to any of these soft tissues can greatly inhibit ranges and types of motion of the arm.

With its complexity, range of motion and extensive use, a fairly common soft tissue injury is damage to the rotator cuff or rotator cuff tendons. Damage to the rotator cuff is a potentially serious medical condition that may occur during hyperextension, from an acute traumatic tear or from overuse of the joint. With its critical role in abduction, rotational strength and torque production, the most common injury associated with the rotator cuff region is a strain or tear involving the supraspinatus tendon. A tear in the supraspinitus tendon 19 is schematically depicted in FIG. 2. A tear at the insertion site of the tendon with the humerus, may result in the detachment of the tendon from the bone. This detachment may be partial or full, depending upon the severity of the injury. Additionally, the strain or tear can occur within the tendon itself. Injuries to the supraspinatus tendon 19 and recognized modalities for treatment are defined by the type and degree of tear. The first type of tear is a full thickness tear as also depicted in FIG. 2, which as the term indicates is a tear that extends through the thickness of the supraspinatus tendon regardless of whether it is completely torn laterally. The second type of tear is a partial thickness tear which is further classified based on how much of the thickness is torn, whether it is greater or less than 50% of the thickness.

The accepted treatment for a full thickness tear or a partial thickness tear greater than 50% includes reconnecting the torn tendon via sutures. For the partial thickness tears greater than 50%, the tear is completed to a full thickness tear by cutting the tendon prior to reconnection. In contrast to the treatment of a full thickness tear or a partial thickness tear of greater than 50%, the treatment for a partial thickness tear less than 50% usually involves physical cessation from use of the tendon, i.e., rest. Specific exercises can also be prescribed to strengthen and loosen the shoulder area. In many instances, the shoulder does not heal and the partial thickness tear can be the source of chronic pain and stiffness. Further, the pain and stiffness may cause restricted use of the limb which tends to result in further degeneration or atrophy in the shoulder. Surgical intervention may be required for a partial thickness tear of less than 50%, however, current treatment interventions do not include repair of the tendon, rather the surgical procedure is directed to arthroscopic removal of bone to relieve points of impingement or create a larger tunnel between the tendon and bone that is believed to be causing tendon damage. As part of the treatment, degenerated tendon may also be removed using a debridement procedure in which tendon material is ablated. Again, the tendon partial tear is not repaired. Several authors have reported satisfactory early post operative results from these procedures, but over time recurrent symptoms have been noted. In the event of recurrent symptoms, many times a patient will "live with the pain". This may result in less use of the aim and shoulder which further causes degeneration of the tendon and may lead to more extensive damage. A tendon repair would then need to be done in a later procedure if the prescribed treatment for partial tear was unsuccessful in relieving pain and stiffness or over time the tear propagated through injury or degeneration to a full thickness tear or a partial thickness tear greater than 50% with attendant pain and debilitation. A subsequent later procedure would include the more drastic procedure of completing the tear to full thickness and suturing the ends of the tendon back together. This procedure requires extensive rehabilitation, has relatively high failure rates and subjects the patient who first presented and was treated with a partial thickness tear less than 50% to a second surgical procedure.

As described above, adequate treatments do not currently exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. Prior damage may result in degeneration that requires a second more drastic procedure to repair the tendon. Further, if the prior procedure was only partially successful in relieving pain and discomfort, a response may be to use the shoulder less which leads to degeneration and increased likelihood of further injury along with the need for more drastic surgery. There is a large need for surgical techniques and systems to treat partial thickness tears of less than 50% and prevent future tendon damage by strengthening or repairing the native tendon having the partial thickness tear.

SUMMARY OF THE INVENTION

According to aspects of the invention, a device for attaching a sheet-like implant to a target tissue is disclosed. In some embodiments, the device includes a pilot member and a staple push rod. In these embodiments, the pilot member has a distal end and at least a pair of prongs extending from the distal end. The prongs are configured to form pilot holes when the distal end of the pilot member is pressed against the target tissue. The staple push rod is disposed within at least a portion of the pilot member and slidable relative thereto. The staple push rod includes at least a pair of stakes. Each stake is dimensioned to engage a surface of a staple to apply pushing forces thereto. Each stake is positioned relative to a prong along an inner surface of the pilot member so that the stakes advance into the pilot holes when the stakes are moved in a distal direction.

In some embodiments of the invention, the stakes are biased to expand against an inner surface of the pilot member. Each stake has a distal portion and a proximal portion. Each distal portion may be dimensioned to extend into a passage defined by a staple. Each proximal portion may have a width larger than a width of each distal portion so that a shoulder of each proximal portion contacts a proximal surface of the staple to apply pushing forces thereto.

In some embodiments, the device also includes a staple which is carried by the staple push rod. The staple includes first and second arms, each having proximal and distal ends. A bridge extends from the proximal end of the first aim to the proximal end of the second arm. A first fluke of the staple has a proximal end abutting the distal end of the first arm. A second fluke of the staple has a proximal end abutting the distal end of the second arm. In some of these embodiments, each stake of the staple push rod has a distal portion and a proximal portion. Each distal portion extends into a passage defined by a fluke. Each proximal portion has a width larger than a width of each distal portion. This allows a shoulder of each proximal portion to contact a distal surface of a fluke to apply pushing forces thereto. The pushing forces place the first arm, the second arm, and the bridge in tension when the flukes are pushed into the target tissue. Each stake may be configured to bend at a location slightly distal of the shoulder when each fluke rotates.

In some embodiments, the proximal portion of each stake has a proximal thickness, and the distal portion of each stake has a distal thickness. The distal thickness may be configured to be less than the proximal thickness to facilitate bending of each stake at a location slightly distal of each shoulder. In some embodiments, each stake bends proximate the proximal end of a fluke when the flukes rotate. The proximal portions of the stakes may be configured with sufficient length so that there is a gap between the staple push rod and the bridge portion of staple. This allows the staple to be placed in tension without the bridge portion of the staple contacting the staple push rod.

In some embodiments, each prong of the pilot member has a length that is greater than a length of each fluke of the staple. The device may be configured such that the pushing forces include a first force applied to a proximal surface of the first fluke at a location that is offset from the first arm. The proximal portions of the stakes may be biased to diverge from one another so that the pushing force applied to each fluke has a laterally outward component. In some embodiments, a distal-most portion of each stake extends across a leading edge of each fluke.

According to aspects of the invention, methods for attaching a sheet-like implant to target tissue are also disclosed. In some embodiments, the methods include the step of providing a device that includes a pilot member. The pilot member has a distal end and at least a pair of prongs extending from the distal end. The device further includes a staple push rod carrying a staple. The staple comprises first and second arms each having proximal and distal ends. A bridge extends from the proximal end of the first arm to the proximal end of the second arm. The staple further comprises a first fluke having a proximal end abutting the distal end of the first arm, and a second fluke having a proximal end abutting the distal end of the second arm. The staple push rod of the device includes a pair of stakes, each having distal and proximal portions. Each distal portion extends into a passage defined by a fluke. Each proximal portion has a width larger than a width of each distal portion so that a shoulder of each proximal portion contacts a distal surface of a fluke.

The above methods further include the step of piercing the target tissue with the first prong of the pilot member to create a first pilot hole, and piercing the target tissue with the second prong to create a second pilot hole. The first fluke is positioned near the first pilot hole and the second fluke is positioned near the second pilot hole. The staple push rod is advanced in a distal direction so that the stakes apply pushing forces to the flukes. This causes the flukes to advance into the pilot holes and causes the first arm, the second arm, and the bridge to be placed in tension. The first arm provides a first reaction force when placed in tension and the second arm provides a second reaction force when placed in tension. The pushing forces and reaction forces cooperate to produce a moment applied to each fluke. The moment applied to each fluke causes each fluke to rotate so that each fluke assumes a locked position. When in the locked position, the longitudinal axis of each fluke is skewed relative to a longitudinal axis of the pilot member.

In some embodiments, a first moment having a first direction is applied to the first fluke, and a second moment having a second direction is applied to the second fluke. In these embodiments, the first direction is different from the second direction. In some embodiments, the first direction is generally opposite the second direction. The first direction may be a clockwise direction while the second direction is a counter-clockwise direction. In some embodiments, a first pushing force is applied to the proximal surface of the first fluke at a location that is offset from the first arm. The first pushing force may be in a direction that is generally parallel to a central axis of the first pilot hole.

In some embodiments, the flukes are advanced into the pilot holes while the prongs are disposed in the pilot holes. The methods may further include the step of moving the pilot member in a proximal direction relative to the target tissue until a distal end of the first prong is located proximal of the first fluke and a distal end of the second prong is located proximally of the second fluke. The step of advancing the staple push rod in a distal direction may include actuating a mechanism that produces relative motion between the staple push rod and the pilot member while applying a distally directed force to the pilot member.

In some of the above embodiments, moving the pilot member in a proximal direction relative to the target tissue includes producing relative motion between the staple push rod and the pilot member while applying a distally directed force to the pilot member. The first fluke may assume a first locking position and the second fluke may assume a second locking position while a distal end of the first prong is located proximal of the first fluke and a distal end of the second prong is located proximally of the second fluke.

According to aspects of the invention, a device for attaching a sheet-like implant to a target tissue is disclosed. In some embodiments the device includes a pilot member, a staple push rod slidably disposed within at least a portion of the pilot member, and a staple carried by the push rod. In these embodiments, the pilot member has a distal end and at least a pair of prongs extending from the distal end. The staple comprises first and second arms, each having proximal and distal ends. A bridge extends from the proximal end of the first aim to the proximal end of the second arm. A first fluke of the staple has a proximal end abutting the distal end of the first arm, and a second fluke of the staple has a proximal end abutting the distal end of the second arm. The staple push rod includes a pair of stakes, each having distal and proximal portions. The distal portion of each stake extends into a passage defined by a fluke. Each proximal portion has a width larger than a width of each distal portion.

With the above arrangement, a shoulder of each proximal portion contacts a distal surface of a fluke to apply pushing forces thereto. The pushing forces place the first arm, the second arm, and the bridge in tension when the flukes are pushed into the target tissue. The first arm provides a first reaction force when placed in tension, and the second arm provides a second reaction force when placed in tension. The pushing forces and the reaction forces cooperate to produce a moment applied to each fluke. The moment applied to each fluke causes each fluke to rotate so that each fluke assumes a locked position. When in the locked position, the longitudinal axis of each fluke is skewed relative to an arm of the staple.

Further aspects of the present invention will become apparent after review of the Detailed Description with reference to the following drawings.

BRIEF DESCRIPTION OF THE DRAWINGS

FIGS. 2A and 2B are alternative perspective views of the tissue fastener or staple of FIG. 1 illustrating other features in accordance with the present disclosure;

FIGS. 4A-4B are partial cross sectional views of the fastener of FIG. 1 depicting a projection in a first retracted state and a second deployed or extended state, respectively;

FIG. 7A, FIG. 7B, and FIG. 7C are multiple plan views illustrating an exemplary staple in accordance with the present detailed description.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

As used herein, the term "tissue" refers to soft tissue, such as a tendon, and/or bone tissue, depending on the context in which it is used.

Figure 1:
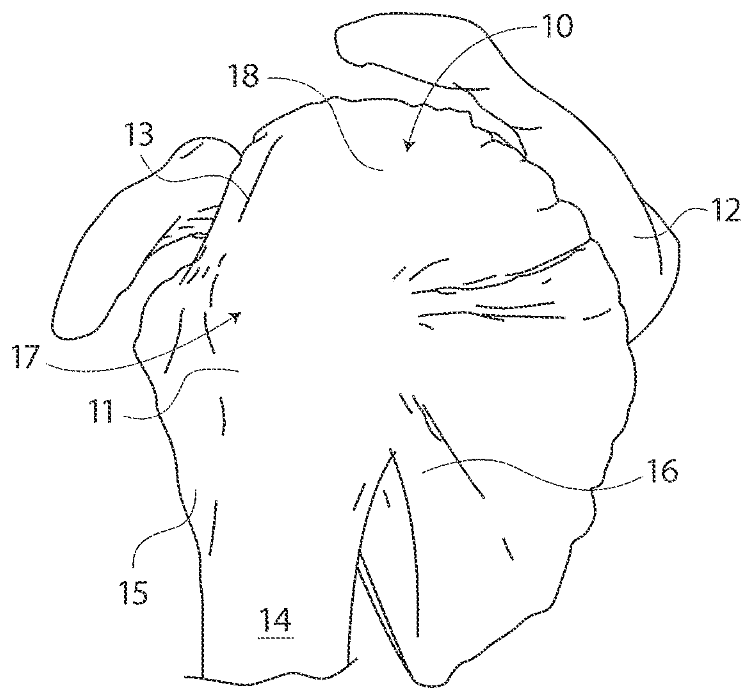
FIG. 1 is a simplified perspective view of the human rotator cuff and associated anatomical structure.
Figure 2:
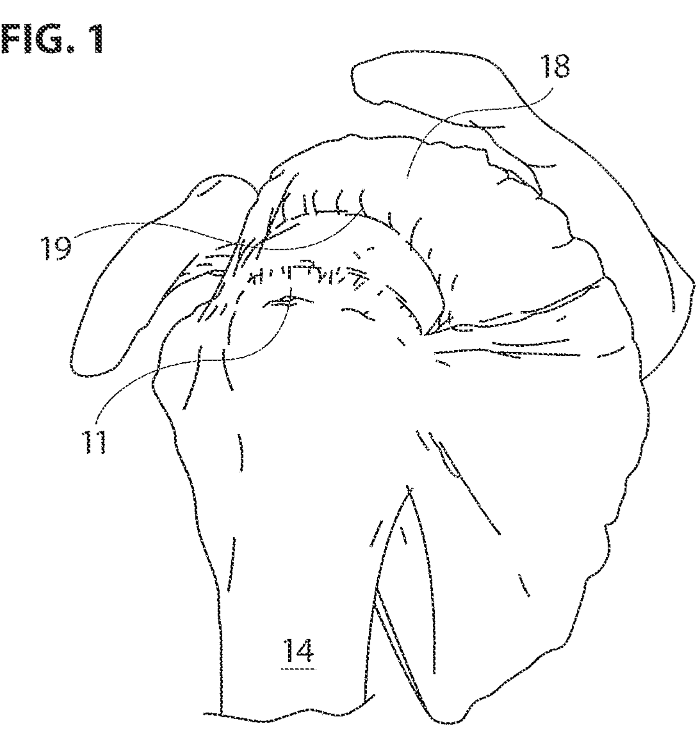
FIG. 2 is a schematic depiction of a full thickness tear in the supraspinatus tendon of the rotator cuff of FIG. 1.
Figure 3:
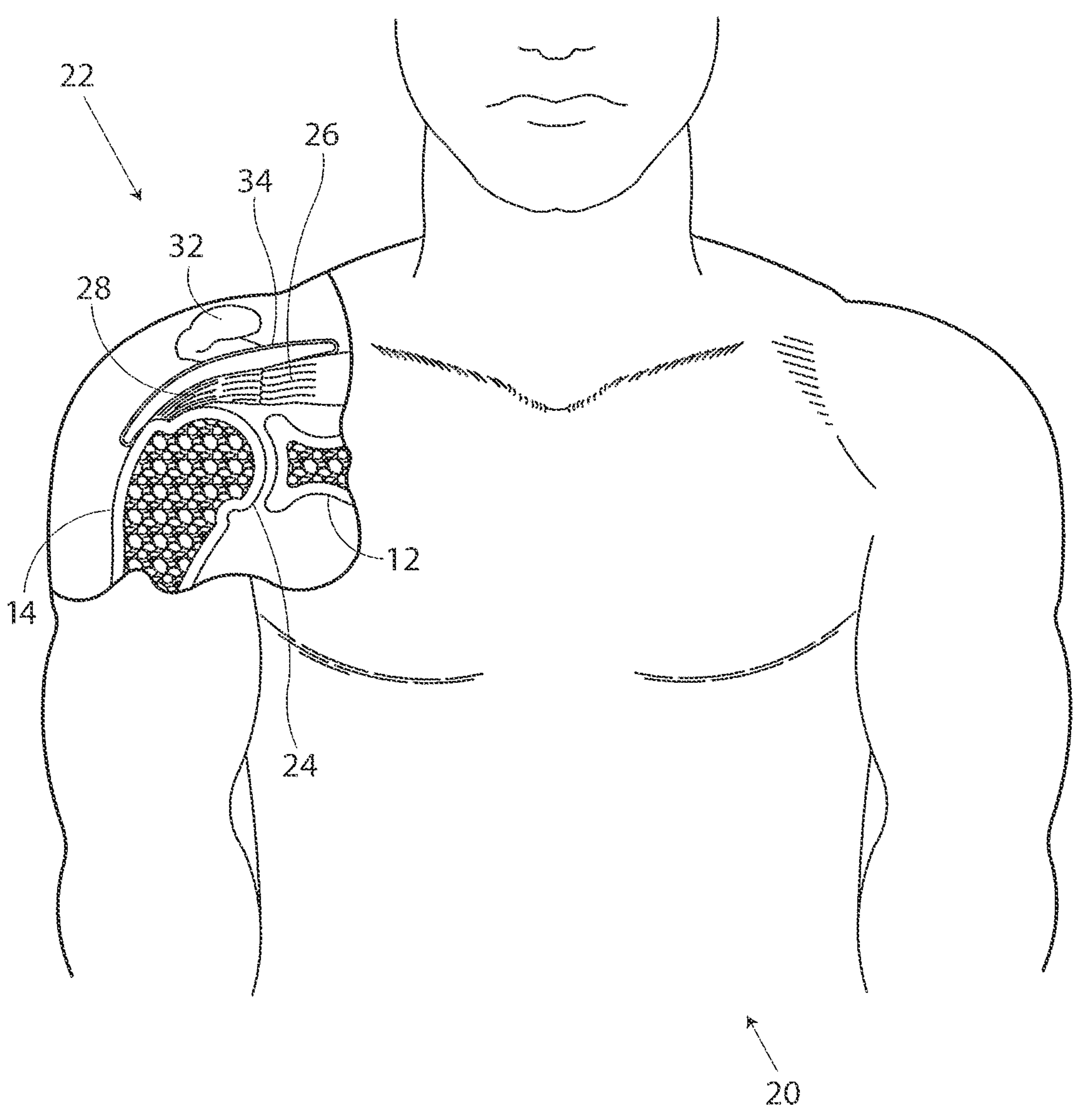
FIG. 3 is a stylized anterior view of a patient with a shoulder of patient being shown in cross-section for purposes of illustration.

FIG. 3 is a stylized anterior view of a patient 20. For purposes of illustration, a shoulder 22 of patient 20 is shown in cross-section in FIG. 3. Shoulder 22 includes a humerus 14 and a scapula 12. In FIG. 3, a head 24 of humerus 14 can be seen mating with a glenoid fossa of scapula 12 at a glenohumeral joint. With reference to FIG. 3, it will be appreciated that the glenoid fossa comprises a shallow depression in scapula 12. The movement of humerus 14 relative to scapula 12 is controlled by a number of muscles including: the deltoid, the supraspinatus, the infraspinatus, the subscapularis, and the *teres* minor. For purposes of illustration, only the supraspinatus 26 is shown in FIG. 3.

With reference to FIG. 3, it will be appreciated that a distal tendon 28 of the supraspinatus 26 meets humerus 14 at an insertion point. Scapula 12 of shoulder 22 includes an acromium 32. In FIG. 3, a subacromial bursa 34 is shown extending between acromium 32 of scapula 12 and head 24 of humerus 14. In FIG. 3, subacromial bursa 34 is shown overlaying supraspinatus 26. Subacromial bursa 34 is one of the hundreds of bursae found the human body. Each bursa comprises a fluid filled sac. The presence of these bursae in the body reduces friction between bodily tissues. Injury and/or infection of the bursa can cause it to become inflamed. This condition is sometimes referred to as bursitis.

The exemplary methods and apparatus described herein may be used to fix tendon repair implants to various target tissues. For example, a tendon repair implant may be fixed to one or more tendons associated with an articulating joint, such as the glenohumeral joint. The tendons to be treated may be torn, partially torn, have internal micro-tears, be untorn, and/or be thinned due to age, injury or overuse. Applicants believe that the methods and apparatus of the present application and related devices may provide very beneficial therapeutic effect on a patient experiencing joint pain believed to be caused by partial thickness tears and/or internal microtears. By applying a tendon repair implant early before a full tear or other injury develops, the implant may cause the tendon to thicken and/or at least partially repair itself, thereby avoiding more extensive joint damage, pain, and the need for more extensive joint repair surgery.

Figure 4:
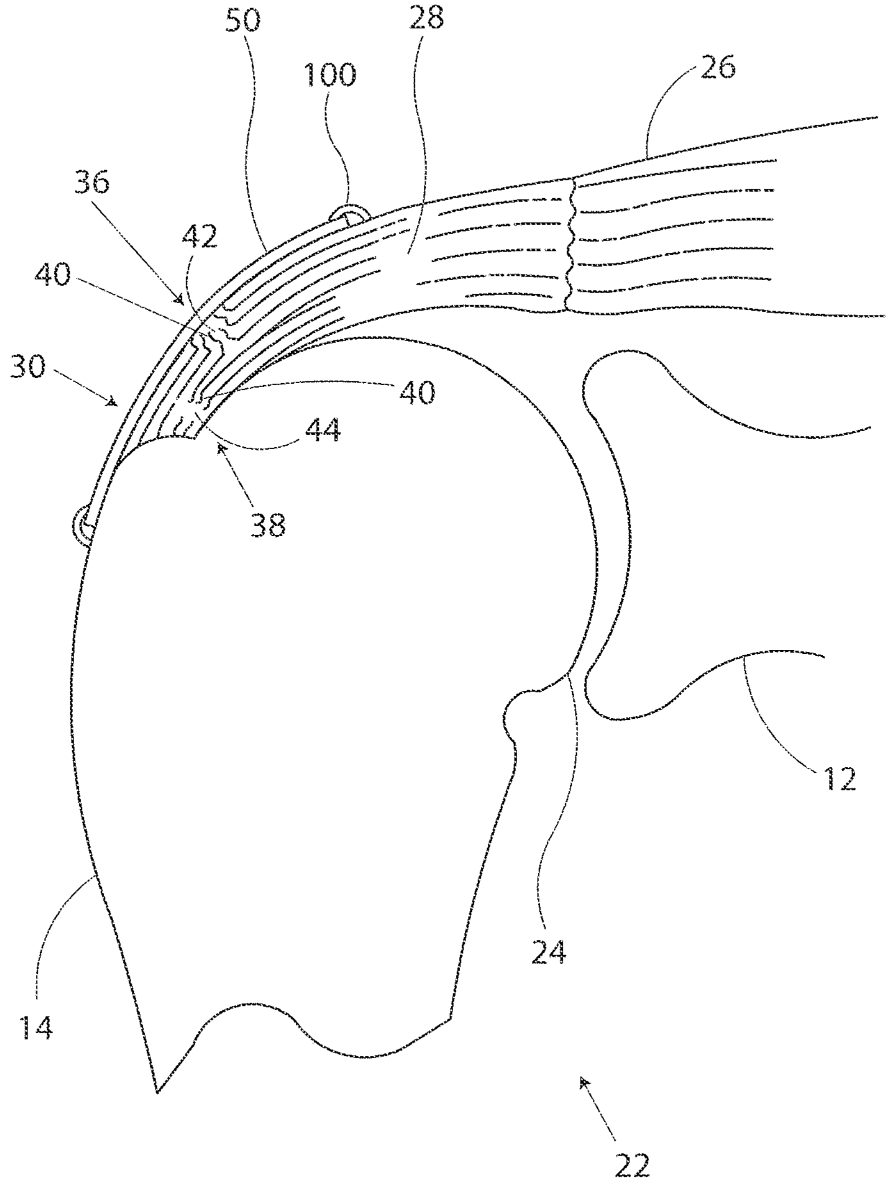
FIG. 4 is a stylized anterior view of a shoulder including a humerus and a scapula. The head of the humerus is shown mating with the glenoid fossa of the scapula at a glenohumeral joint and a sheet-like material is fixed to the tendon.

FIG. 4 is a stylized anterior view of a shoulder 22 including a humerus 14 and a scapula 12. In FIG. 4, a head 24 of humerus 14 is shown mating with a glenoid fossa of scapula 12 at a glenohumeral joint. A supraspinatus 26 is also shown in FIG. 4. This muscle (along with others) control the movement of humerus 14 relative to scapula 12. A distal tendon 28 of supraspinatus 26 meets humerus 14 at an insertion point 30.

In the embodiment of FIG. 4, distal tendon 28 includes a first damaged portion 36. A number of loose tendon fibers 40 in first damaged portion 36 are visible in FIG. 4. First damaged portion 36 includes a first tear 42 extending partially through distal tendon 28. First tear 42 may therefore be referred to as a partial thickness tear. With reference to FIG. 4, it will be appreciated that first tear 42 begins on the side of distal tendon 28 facing the subacromial bursa (shown in the previous Figure) and ends midway through distal tendon 28. Accordingly, first tear 42 may be referred to as a bursal side tear.

With reference to FIG. 4, it will be appreciated that distal tendon 28 includes a second damaged portion 38 located near insertion point 30. In the embodiment of FIG. 4, second damaged portion 38 of distal tendon 28 has become frayed and a number of loose tendon fibers 40 are visible in FIG. 4. Second damaged portion 38 of distal tendon 28 includes second tear 44. With reference to FIG. 4, it will be appreciated that second tear 44 begins on the side of distal tendon 28 facing the humerus 14. Accordingly, second damaged portion 38 may be referred to as an articular side tear.

In the embodiment of FIG. 4, a sheet-like implant 50 has been placed over the bursal side of distal tendon 28. With reference to FIG. 4, it will be appreciated that sheet-like implant 50 extends over insertion point 30, first tear 42 and second tear 44. Some useful methods in accordance with this detailed description may include placing a tendon repair implant on the bursal side of a tendon regardless of whether the tears being treated are on the bursal side, articular side or within the tendon. In some cases the exact location and nature of the tears being treated may be unknown. A tendon repair implant may be applied to the bursal side of a tendon to treat shoulder pain that is most likely caused by one or more partial thickness tears in the tendon. In the embodiment of FIG. 4, sheet-like implant 50 is fixed to distal tendon 28 and to humerus 14 by a plurality of staples 100 as described herein in detail.

Figure 5:
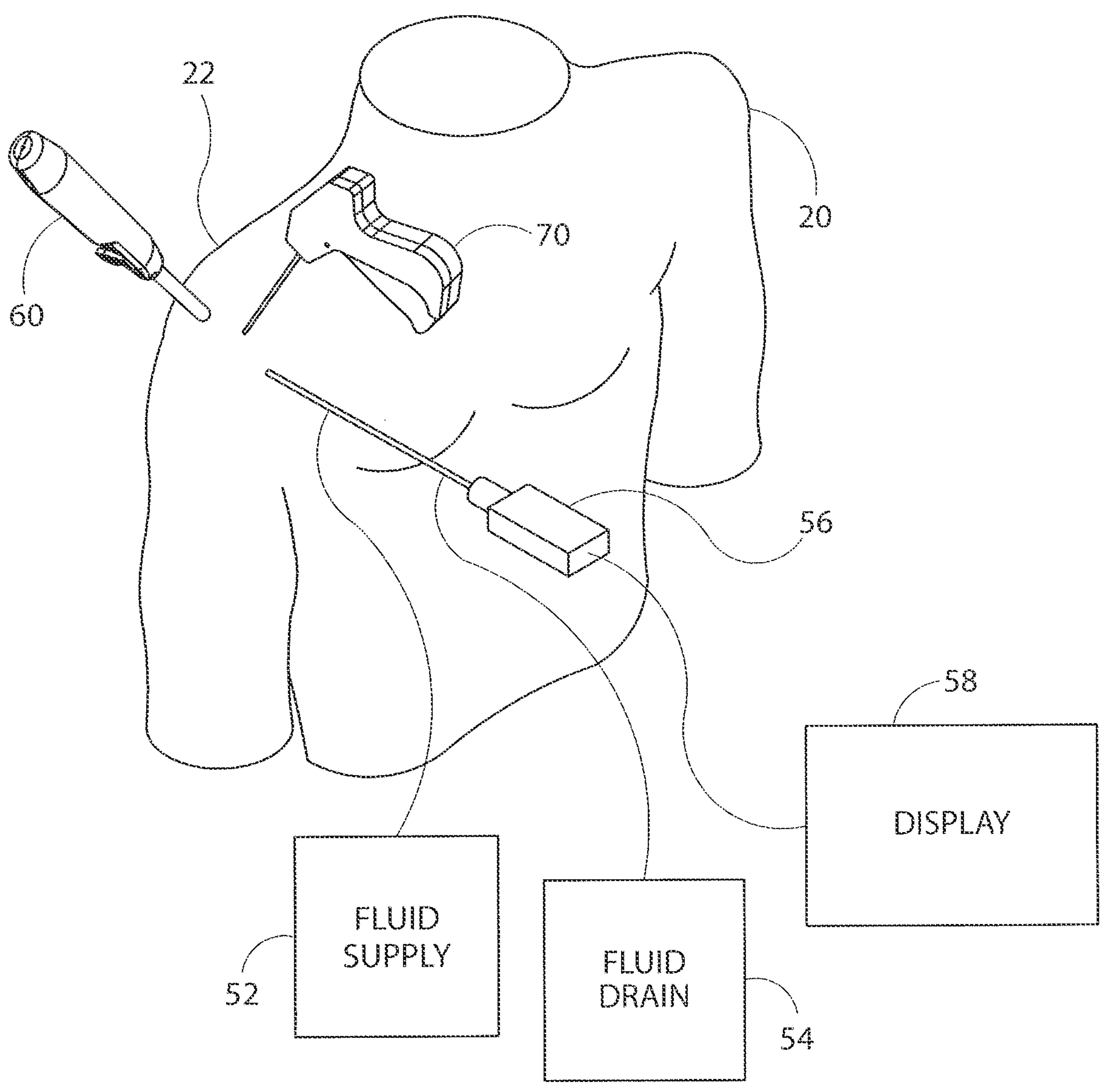
FIG. 5 is a stylized perspective view illustrating an exemplary procedure for treating a shoulder of a patient.

FIG. 5 is a stylized perspective view illustrating an exemplary procedure for treating a shoulder 22 of a patient 20. The procedure illustrated in FIG. 5 may include, for example, fixing tendon repair implants to one or more tendons of shoulder 22. The tendons treated may be torn, partially torn, have internal micro-tears, be untorn, and/or be thinned due to age, injury or overuse.

Shoulder 22 of FIG. 5 has been inflated to create a cavity therein. In the exemplary embodiment of FIG. 5A, a fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be fixed to a bursal surface of the tendon regardless of whether there are visible signs of tendon damage. Applicants believe that the methods and apparatus of the present application and related devices may provide very beneficial therapeutic effect on a patient experiencing joint pain believed to be caused by internal microtears, but having no clear signs of tendon tears. By applying a tendon repair implant early before a full tear or other injury develops, the implant may cause the tendon to thicken and/or at least partially repair itself, thereby avoiding more extensive joint damage, pain, and the need for more extensive joint repair surgery.

A delivery system 60 can be seen extending from shoulder 22 in FIG. 5. Delivery system 60 comprises a sheath that is fixed to a handle. The sheath defines a lumen and a distal opening fluidly communicating the lumen. In the embodiment of FIG. 5, the distal opening of the sheath has been placed in fluid communication with the cavity created in shoulder 22.

A tendon repair implant is at least partially disposed in the lumen defined by the sheath of delivery system 60. Delivery system 60 can be used to place the tendon repair implant inside shoulder 22. Delivery system 60 can also be used to hold the tendon repair implant against the tendon. In some embodiments, the tendon repair implant is folded into a compact configuration when inside the lumen of the sheath. When this is the case, delivery system 60 may be used to unfold the tendon repair implant into an expanded shape.

The tendon repair implant may be fixed to the tendon while it is held against the tendon by delivery system 60. Various attachment elements may be used to fix the tendon repair implant to the tendon. Examples of attachment elements that may be suitable in some applications include sutures, tissue anchors, bone anchors, and staples. In the exemplary embodiment of FIG. 5, the shaft of a fixation tool 70 is shown extending into shoulder 22. In one exemplary embodiment, fixation tool 70 is capable of fixing the tendon repair implant to the tendon with one or more staples while the tendon repair implant is held against the tendon by delivery system 60.

Figure 6:
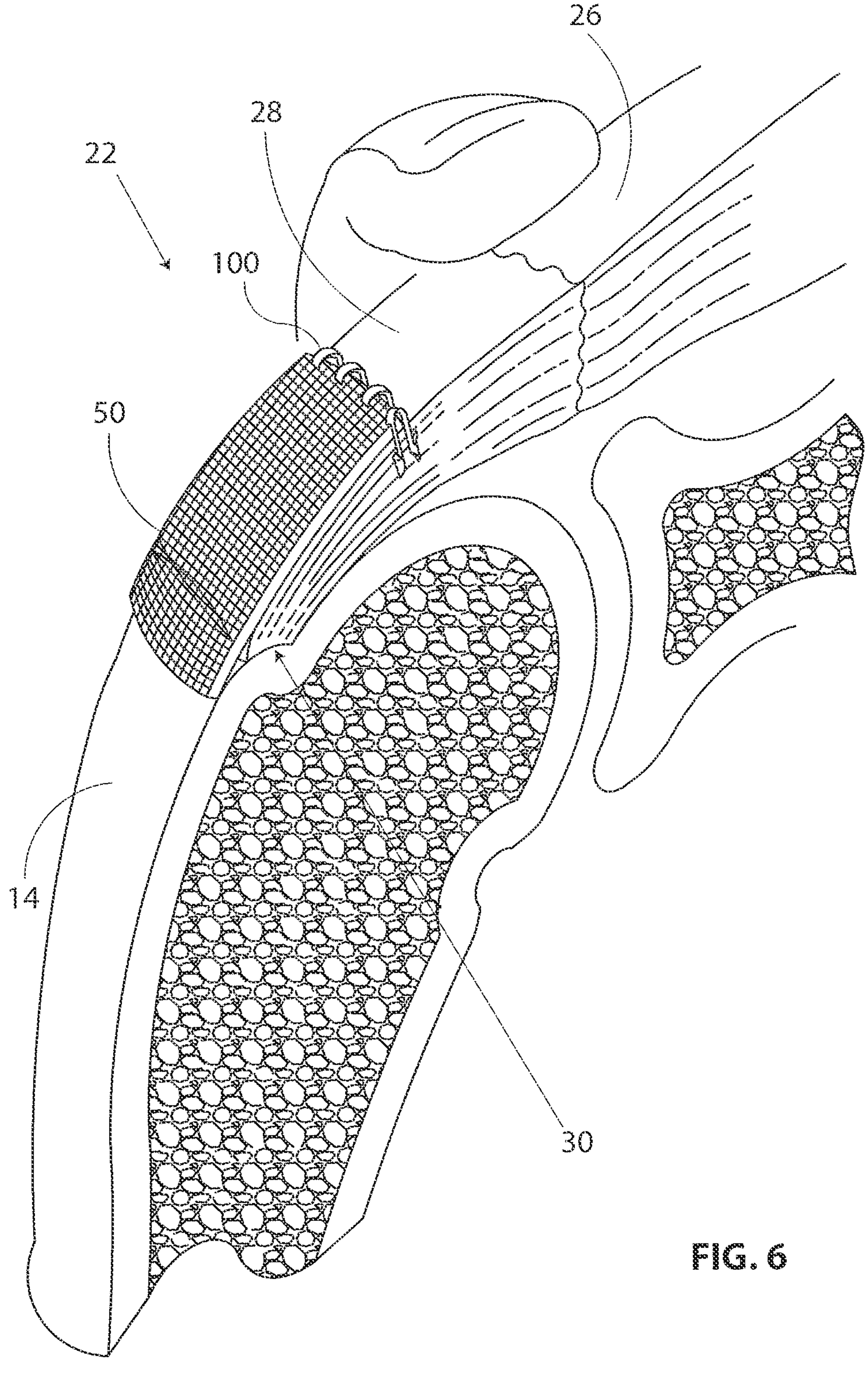
FIG. 6 is a stylized perspective view of a shoulder including a supraspinatus having a distal tendon with a sheet-like material fixed thereto. A proximal end of the supraspinatus is fixed to the scapula and the distal tendon of the supraspinatus is fixed to the humerus.

FIG. 6 is a stylized perspective view of a shoulder 22 including a supraspinatus 26 having a distal tendon 28. With reference to FIG. 6, it will be appreciated that a tendon repair implant 50 has been fixed to a surface of distal tendon 28. Tendon repair implant 50 may comprise, for example, various sheet-like structures without deviating from the spirit and scope of the present detailed description. In some useful embodiments, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications including weaving, knitting, and braiding. In some embodiment, the sheet-like structure may comprise a laminate including multiple layers of film with each layer of film defining a plurality of micro-machined or formed holes. The sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Freemont, Calif. which identifies these materials using the trademark BIOMATERIAL.™.

Various attachment elements may be used to fix tendon repair implant 50 to distal tendon 28 without deviating from the spirit and scope of this detailed description. Examples of attachment elements that may be suitable in some applications include sutures, tissue anchors, bone anchors, and staples. In the exemplary embodiment of FIG. 6, a plurality of staples 100 are fixing tendon repair implant 50 to distal tendon 28. In some exemplary methods, a plurality of staples 100 may be applied using a fixation tool. The fixation tool may then be withdrawn from the body of the patient. Distal tendon 28 meets humerus 14 at an insertion point 30. With reference to FIG. 6, it will be appreciated that sheet-like implant 50 extends over insertion point 30. Tendon repair implant may be applied to distal tendon 28, for example, using the procedure illustrated in the previous Figure.

FIG. 7A, FIG. 7B, and FIG. 7C are multiple plan views illustrating an exemplary staple 100 in accordance with the present detailed description. FIG. 7A, FIG. 7B, and FIG. 7C may be collectively referred to as FIG. 7. A proximal direction is illustrated with an arrow P in FIG. 7. A distal direction is illustrated with a second arrow D in FIG. 7.

Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. Similarly, the distal end of second arm 102B abuts the proximal end of a second fluke 106B. In FIG. 7, first fluke 106A and second fluke 106B are shown extending distally from first arm 102A and second arm 102B, respectively. With reference to FIG. 7, it will be appreciated that first fluke 106A has a lateral extent that is larger than a lateral extent of first arm 102A. First fluke 106A is mounted eccentrically to first arm 102A in the embodiment of FIG. 7. Second fluke 106B is mounted eccentrically to second arm 102B and second fluke 106B has a lateral extent that is larger than a lateral extent of second arm 102B. First fluke 106A includes a first proximal surface 108A projecting at an outward angle in a proximal direction away from the distal end of first arm 102A. Second fluke 106B includes a second proximal surface 108B projecting at an outward angle in a proximal direction away from the distal end of second arm 102B.

With reference to FIG. 7A, it will be appreciated that first fluke 106A includes a first point 120A and a first barb 122A. Second fluke 106B includes a second point 120B and a second barb 122B. In FIG. 7, first point 120A and second point 120B are shown generally pointing in the distal direction indicated by arrow D. Also in FIG. 7, first barb 122A and second barb 122B are shown generally pointing in the proximal direction indicated by arrow P.

With reference to FIG. 7A it will be appreciated that first fluke 106A defines a first passageway 124A and second fluke 106B defines a second passageway 124B. In the exemplary embodiment of FIG. 7, first passageway 124A extends through first fluke 106A and second passageway 124B extends through second fluke 106B. It will be appreciated, however, that first passageway 124A may extend through other portions of staple 100 in some embodiments. Similarly, second passageway 124B may extend through other portions of staple 100 in some embodiments. With reference to FIG. 7B it will be appreciated that, first passageway 124A and second passageway 124B each have a generally square cross-sectional shape. It will be appreciated, however, that first passageway 124A and second passageway 124B may have various cross-sectional shapes without deviating from the spirit and scope of the present detailed description. Further, each passageway can extend partially through the length of each fluke rather than all the way through to provide a cavity rather than a passageway.

With reference to FIG. 7C, it will be appreciated that first barb 122A of first fluke 106A defines a first notch 126A. In the exemplary embodiment of FIG. 7, first notch 126A divides first barb 122A into a first sub-barb and a second sub-barb. Second barb 122B of second fluke 106B defines a second notch 126B. In the exemplary embodiment of FIG. 7, second notch 126B divides second barb 122B into a first sub-barb and a second sub-barb.

Figure 8:
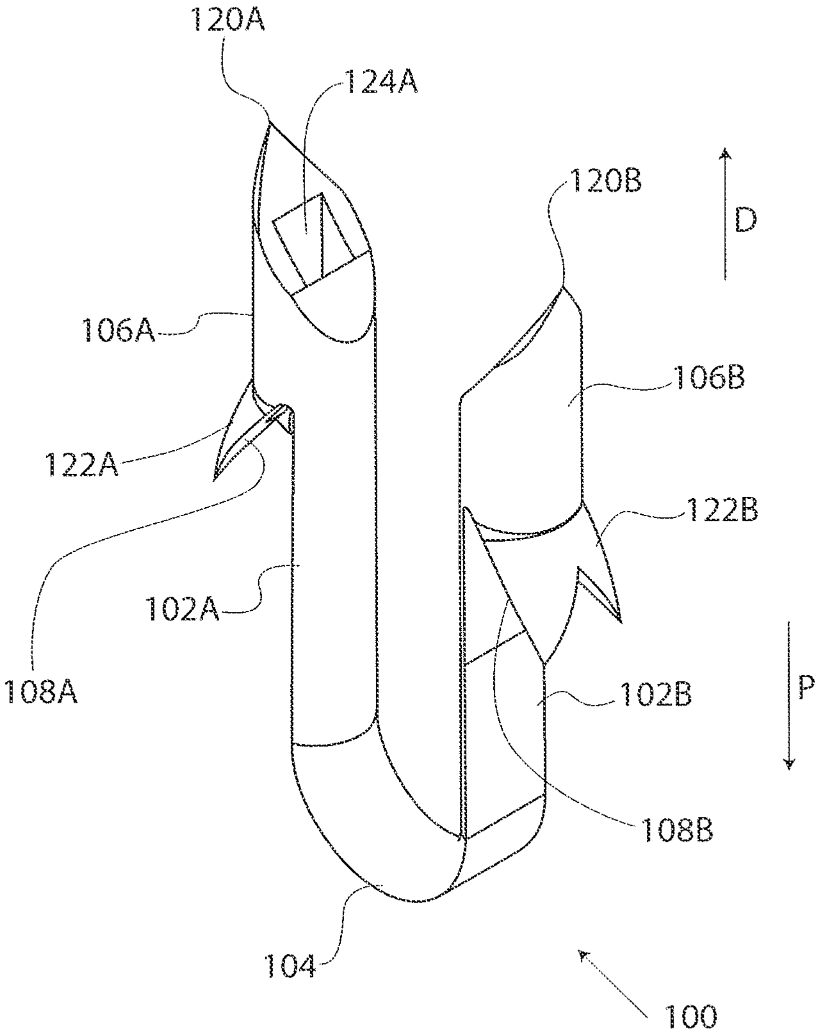
FIG. 8 is a perspective view further illustrating the staple shown in the previous Figure.

FIG. 8 is a perspective view showing staple 100 shown in the previous Figure. Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. With reference to FIG. 8 it will be appreciated that first fluke 106A defines a first passageway 124A. In the exemplary embodiment of FIG. 8, first passageway 124A has a generally square cross-sectional shape. It will be appreciated, however, that first passageway 124A may have various cross-sectional shapes without deviating from the spirit and scope of the present detailed description.

A second fluke 106B extends distally from second arm 102B with the proximal end of second fluke 106B abutting the distal end of second arm 102B. With reference to FIG. 8, it will be appreciated that second fluke 106B has a lateral extent that is larger than a lateral extent of second arm 102B. Second fluke 106B is mounted eccentrically to second arm 102B in the embodiment of FIG. 8. Similarly, first fluke 106A is mounted eccentrically to first arm 102A and first fluke 106A has a lateral extent that is larger than a lateral extent of first arm 102A.

A proximal direction is illustrated with an arrow P in FIG. 8. A distal direction is illustrated with a second arrow D in FIG. 8. With reference to FIG. 8A, it will be appreciated that first fluke 106A of first arm 102A includes a first point 120A and a first barb 122A. Second fluke 106B includes a second point 120B and a second barb 122B. In FIG. 8, first point 120A and second point 120B are shown generally pointing in the distal direction indicated by arrow D. Also in FIG. 8, first barb 122A and second barb 122B are shown generally pointing in the proximal direction indicated by arrow P. With reference to FIG. 8, it will be appreciated that first fluke 106A includes a first proximal surface 108A projecting at an outward angle in a proximal direction away from the distal end of first arm 102A. Second fluke 106B includes a second proximal surface 108B projecting at an outward angle in a proximal direction away from the distal end of second arm 102B.

Figure 9:
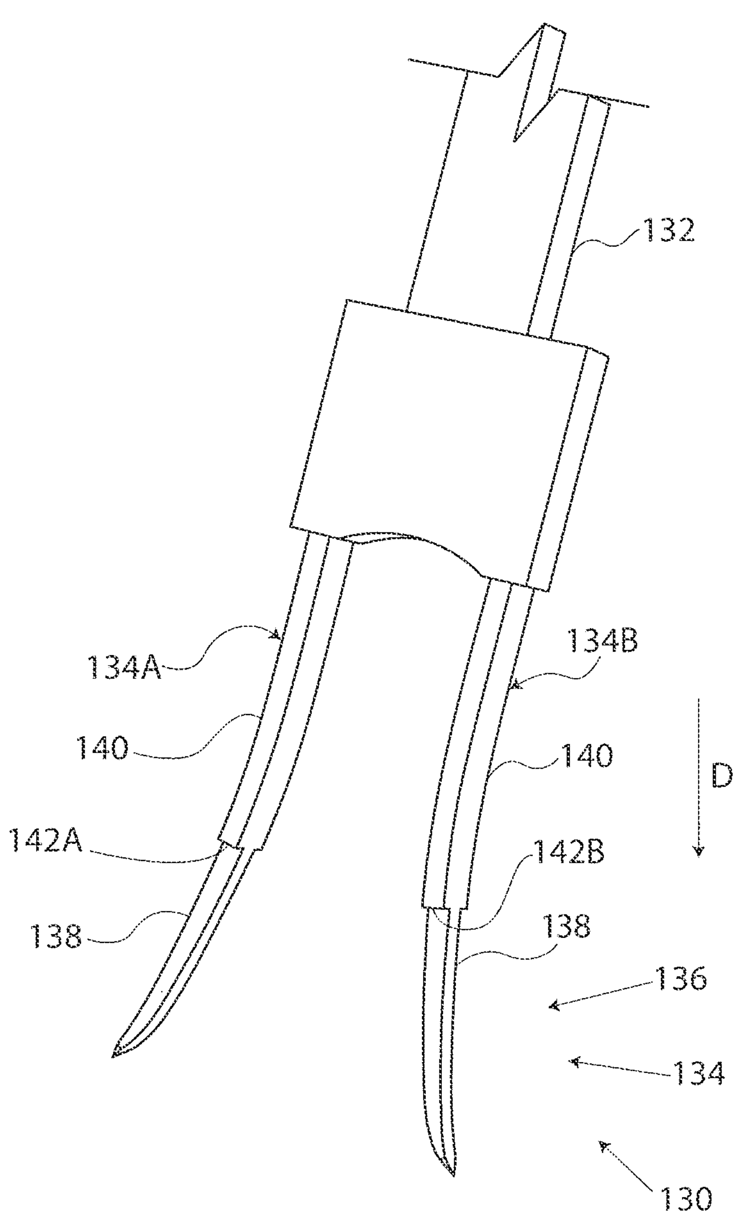
FIG. 9 is a perspective view showing a staple push rod that may be used in conjunction with the staple shown in the previous Figure.

FIG. 9 is a perspective view showing a staple push rod 130 that may be used in conjunction with staple 100 shown in the previous Figure. Staple push rod 130 includes a shaft 132 and a pair of stakes 134 extending distally beyond a distal end of shaft 132. The distal direction is indicated with an arrow D in FIG. 9. Stakes 134 include a first stake 134A and a second stake 134B. First stake 134A and second stake 134B form a fork 136.

In the embodiment of FIG. 9, each stake 134 has a distal portion 138 and a proximal portion 140. In some useful embodiments, each distal portion 138 is dimensioned to extend into a passage defined by a staple. In the embodiment of FIG. 9, each proximal portion 140 has a width larger than a width of each distal portion 138 so that a shoulder of each proximal portion 140 contacts a proximal surface of the staple to apply pushing forces thereto. First stake 134A comprises a first shoulder 142A and second stake 134B comprises a second shoulder 142B. Although depicted as a shoulder to provide pushing force to the staple, other designs can be utilized. For example, any larger cross section proximal portion can provide a pushing force, such as a conical increase in profile. In the embodiment of FIG. 9, proximal portion 140 of first stake 134A and the proximal portion 140 of second stake 134B diverge from one another as they extend in distal direction D away from shaft 132. In some applications, this arrangement may cause pushing forces applied to two flukes of a staple to have a laterally outward component.

In FIG. 9, first stake 134A and second stake 134B are shown assuming a substantially unstressed state. It will be appreciated that first stake 134A and second stake 134B can be resiliently urged to assume shapes other than the shape shown in FIG. 9. For example, first stake 134A and second stake 134B may be urged together so that fork 136 can be inserted into a lumen having a diameter smaller than the distance between the distal points of first stake 134A and second stake 134B shown in FIG. 9.

Figures 10A, 10B:
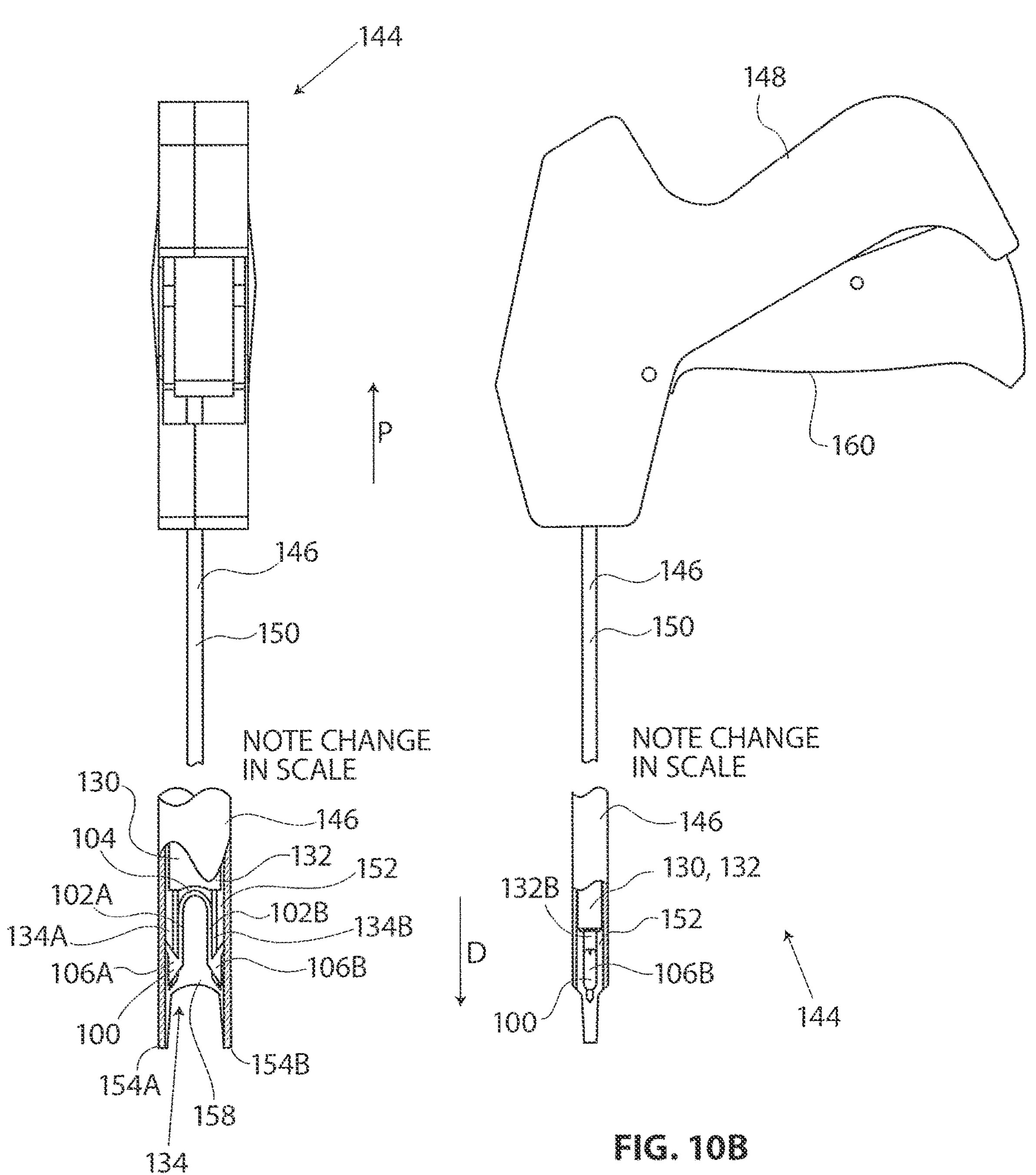
FIG. 10A and FIG. 10B illustrate multiple plan views of an exemplary fixation tool in accordance with the present detailed description.

FIG. 10A and FIG. 10B illustrate multiple plan views of an exemplary fixation tool 144 in accordance with the present detailed description. Fixation tool 144 incorporates staple push rod 130 and is useful in delivering staple 100. FIG. 10A and FIG. 10B may be referred to collectively as FIG. 10. It is customary to refer to multiview projections using terms such as front view, top view, and side view. In accordance with this convention, FIG. 10A may be referred to as a top view of fixation tool 144 and FIG. 10B may be referred to as a side view of fixation tool 144. The terms top view and side view are used herein as a convenient method for differentiating between the views shown in FIG. 10. It will be appreciated that the elements shown in FIG. 10 may assume various orientations without deviating from the spirit and scope of this detailed description. Accordingly, the terms top view and side view should not be interpreted to limit the scope of the invention recited in the attached claims.

In the embodiment of FIG. 10, fixation tool 144 comprises a pilot member or fixation tool shaft 146 that is attached to a handle 148. Fixation tool shaft 146 comprises a wall 150 defining a lumen 152. With reference to FIG. 10, it will be appreciated that fixation tool shaft 146 includes a first prong 154A and a second prong 156B that extend distally beyond a distal end 158 of lumen 152.

In FIG. 10, a staple 100 can be seen residing in lumen 152 of fixation tool shaft 146. For purposes of illustration, a distal portion of fixation tool shaft 146 is enlarged in FIG. 10 to better show staple 100. Staple 100 comprises a first aim 102A, a second arm 102B, and a bridge 104 extending from the proximal end of first arm 102A to the proximal end of second arm 102B. The distal end of first arm 102A abuts the proximal end of a first fluke 106A. Similarly, the distal end of second arm 102B abuts the proximal end of a second fluke 106B. In FIG. 10, first fluke 106A and second fluke 106B are shown extending distally from first arm 102A and second arm 102B, respectively.

Staple push rod 130 includes a shaft 132 and a pair of stakes 134 extending distally beyond a distal end of shaft 132. The distal direction is indicated with an arrow D in FIG. 10. Stakes 134 include a first stake 134A and a second stake 134B. In FIG. 10, a distal portion of each stake 134 can be seen extending through a passageway defined by staple 100. In the embodiment of FIG. 10, a trigger 160 is pivotably coupled to handle 148 of fixation tool 144. Trigger 160 is operatively coupled to staple push rod 130. In operation, staple push rod 130 will be advanced and/or retracted in an axial direction when trigger 160 is pivoted relative to handle 148.

Figure 11A:
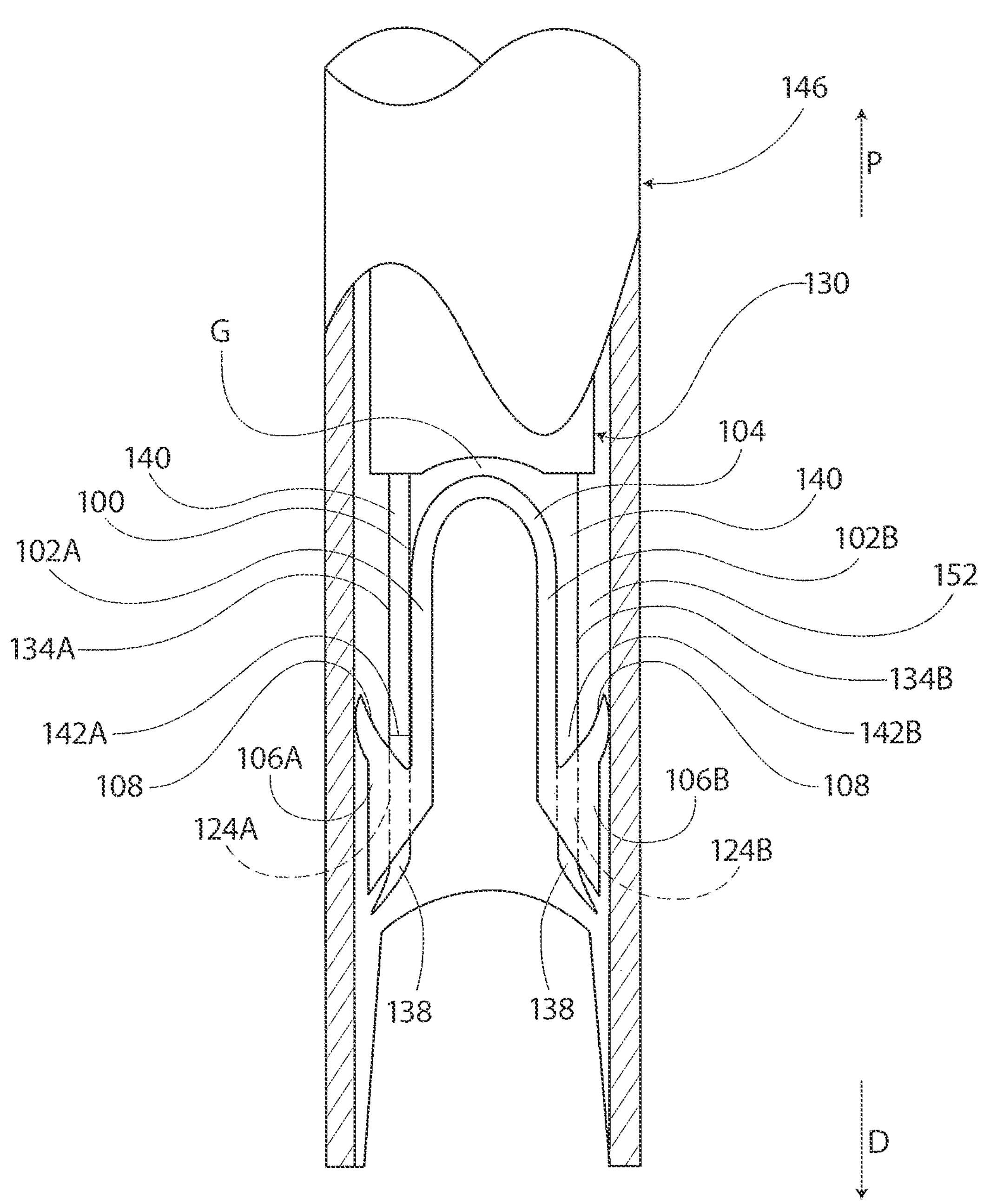
FIG. 11A is a further enlarged partial cross-sectional view of a distal portion of the fixation tool shaft shown in the previous Figure.

FIG. 11A is a further enlarged top view of a distal portion of fixation tool shaft 146 shown in the previous Figure. For purposes of illustration, fixation tool shaft 146 is shown in partial cross-section in FIG. 11A so that staple 100 is visible residing in lumen 152. With reference to FIG. 11A, it will be appreciated that staple 100 is disposed on a distal portion of staple push rod 130. Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. Similarly, the distal end of second arm 102B abuts the proximal end of a second fluke 106B. In FIG. 11, first fluke 106A and second fluke 106B are shown extending distally from first arm 102A and second aim 102B, respectively.

First fluke 106A of staple 100 defines a first passageway 124A. In FIG. 11A, a distal portion 138 of first stake 134A of staple push rod 130 can be seen extending through first passageway 124A defined by first fluke 106A. A distal portion 138 of second stake 134B of staple push rod 130 can be seen extending through a second passageway 124B defined by second fluke 106B of staple 100.

In FIG. 11A, a first shoulder 142A of first stake 134A is shown contacting proximal surface 108 of first fluke. Distal portion 138 of first stake 134A extends distally of first shoulder 142A and proximal portion 140 of first stake 134A extends proximally of first shoulder 142A. In some useful embodiments, the proximal portion of first stake 134A has a first thickness and the distal portion of first stake 134A has a second thickness different from the first thickness. In some particularly useful embodiments, the second thickness is less than the first thickness. In some applications, this may increase the flexibility of the distal portion of first stake 134A so that it bends more easily, and so that it withdraws from the staple with minimal force.

A second shoulder 142B of second stake 134B is shown contacting proximal surface 108 of second fluke 106 in FIG. 11A. A distal portion 138 of second stake 134B extends distally of second shoulder 142B and a proximal portion 140 of second stake 134B extends proximally of second shoulder 142B. In some useful embodiments, the proximal portion of second stake 134B has a first thickness and the distal portion of second stake 134B has a second thickness different from the first thickness. In some particularly useful embodiments, the second thickness is less than the first thickness. In some applications, this may increase the flexibility of the distal portion of first stake 134A so that it bends more easily, and so that it withdraws from the staple with minimal force.

With reference to FIG. 11A, it will be appreciated that there is a gap G between staple push rod 130 and bridge 104 of staple 100. In some applications, gap G allows staple 100 to be placed in tension without bridge 104 contacting staple push rod 130. Staple 100 may be placed in tension, for example, as staple 100 is advanced into a target tissue.

Figure 11B:
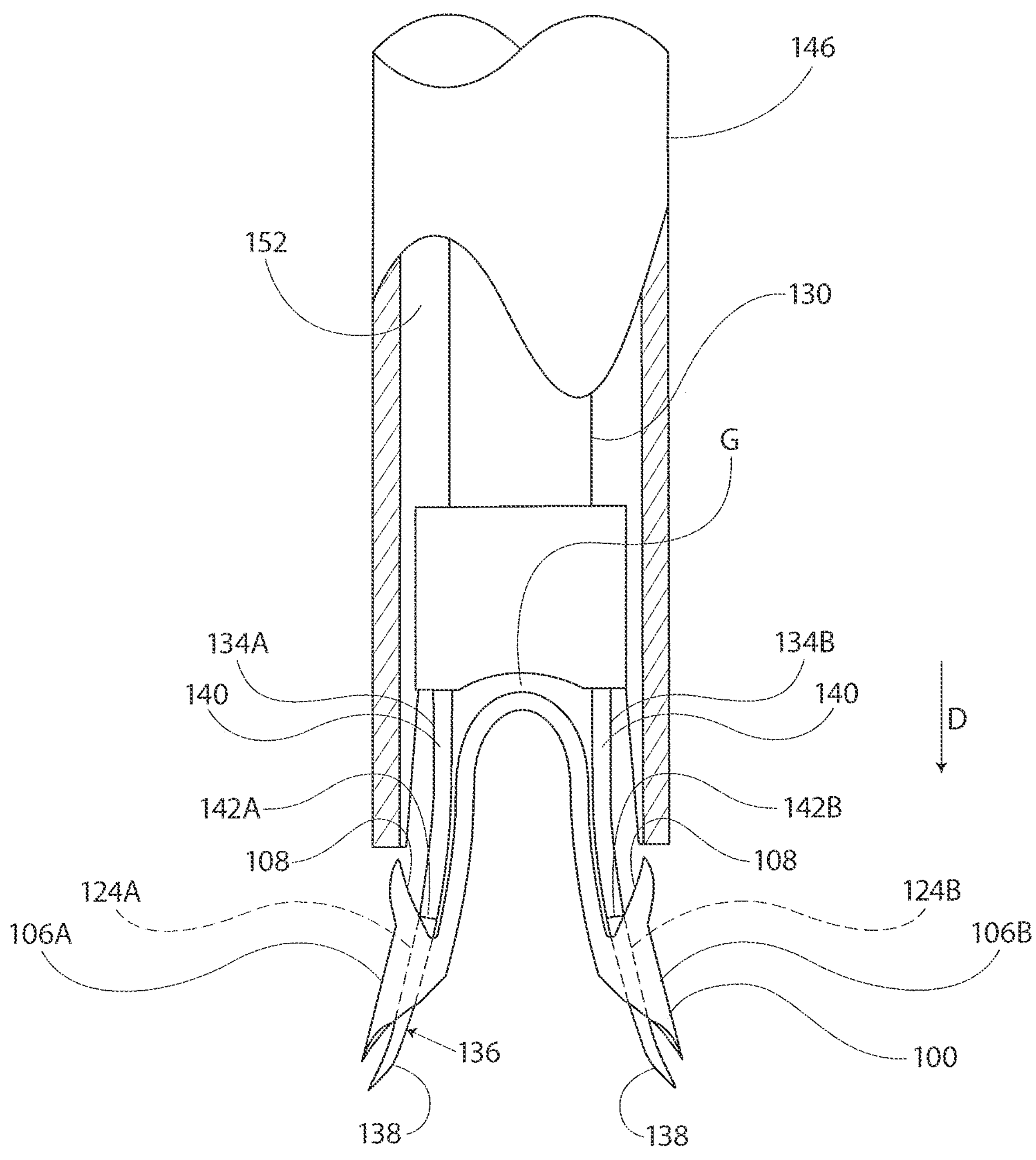
FIG. 11B is an additional partial cross-sectional view showing a staple carried by a staple push rod and a fixation tool shaft disposed about the staple push rod.

FIG. 11B is an additional top view showing a distal portion of fixation tool shaft 146, staple push rod 130, and staple 100. By comparing FIG. 11A and FIG. 11B, it will be appreciated that staple push rod 130 and staple 100 have been advanced in a distal direction D relative to fixation tool shaft 146. In FIG. 11B, staple 100 is shown extending out of lumen 152 defined by fixation tool shaft 146.

In FIG. 11B, a distal portion 138 of first stake 134A of staple push rod 130 can be seen extending through a first passageway 124A defined by first fluke 106A of staple 100. In FIG. 11B, a first shoulder 142A of first stake 134A is shown contacting proximal surface 108 of first fluke 106A. Distal portion 138 of first stake 134A extends distally of first shoulder 142A and proximal portion 140 of first stake 134A extends proximally of first shoulder 142A. In some useful embodiments, the proximal portion of first stake 134A has a first width and the distal portion of first stake 134A has a second width different from the first width. In some particularly useful embodiments, the first width is greater than the first width. The arrangement allows the proximal portion of stake to engage a proximal surface of the staple to apply pushing forces to the staple.

In FIG. 11B, a distal portion 138 of second stake 134B of staple push rod 130 can be seen extending through a second passageway 124B defined by second fluke 106B of staple 100. In FIG. 11B, a second shoulder 142B of second stake 134B is shown contacting proximal surface 108 of second fluke 106B. In the embodiment of FIG. 11B, proximal portion 140 of second stake 134B may apply pushing force to proximal surface 108 of second stake 134B. Proximal portion 140 of second stake 134B extends proximally of second shoulder 142B and distal portion 138 of second stake 134B extends distally of second shoulder 142B. In the embodiment of FIG. 11B, proximal portion 140 of second stake 134B has a width larger than the width of distal portion 138 of second stake 134B so that the shoulder 142 of second stake 134B contacts proximal surface 108 of second fluke 106B to apply pushing forces thereto.

In the embodiment of FIG. 11B, first stake 134A and second stake 134B are in a substantially unstressed state. It will be appreciated that first stake 134A and second stake 134B can be resiliently urged to assume shapes other than the shape shown in FIG. 11. For example, first stake 134A and second stake 134B may be urged together so that fork 136 of staple push rod 130 and staple 100 can be inserted into lumen 152 defined by fixation tool shaft 146.

With reference to FIG. 11B, it will be appreciated that there is a gap G between staple push rod 130 and bridge 104 of staple 100. In some applications, gap G allows staple 100 to be placed in tension without bridge 104 contacting staple push rod 130. In some applications, placing staple 100 under tension may urge first fluke 106 and second fluke 106 into orientations which lock staple 100 into a target tissue. For example, first fluke 106A and second fluke 106B may be rotated so that a barb of each fluke engages the target tissue. When this is the case, the tension on the staple may keep first fluke 106A and second fluke 106B in the rotated position. Also when this is the case, the barbs of the rotated flukes may inhibit staple pullout.

Figures 12A, 12B, 12C:
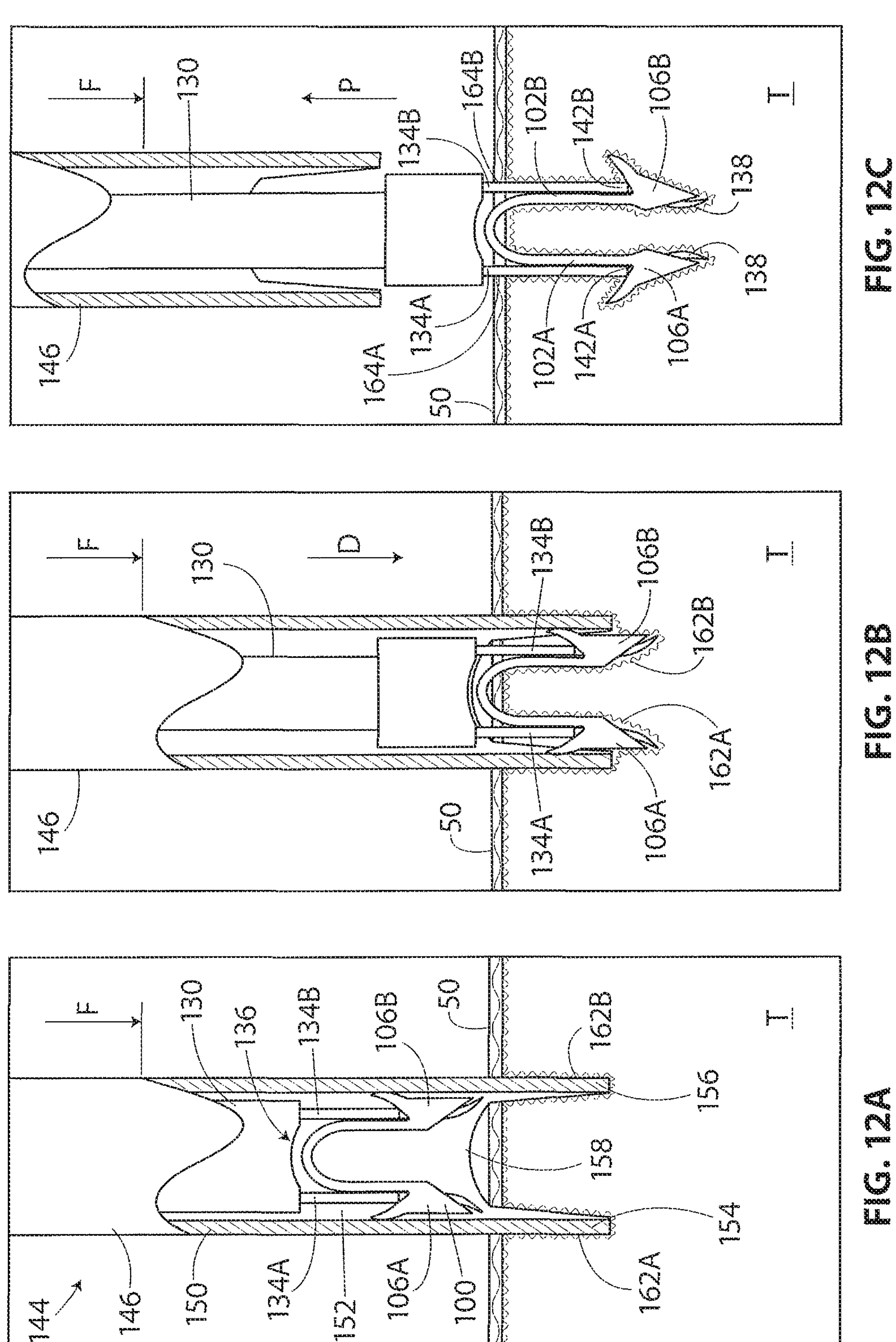
FIG. 12A through FIG. 12C are a sequence of plan views illustrating an exemplary method and apparatus in accordance with the present detailed description.

FIG. 12A through FIG. 12C are a sequence of plan views illustrating an exemplary method in accordance with the present detailed description. FIG. 12A, FIG. 12B, and FIG. 12C may be collectively referred to as FIG. 12. The exemplary method illustrated in FIG. 12 may be used, for example, to fix a tendon repair implant 50 to a target tissue T using a staple 100.

At FIG. 12A, a fixation tool 144 has been used to form a first pilot hole 162A and a second pilot hole 162B in target tissue T. In the embodiment of FIG. 12, fixation tool 144 includes a fixation tool shaft 146 comprising a wall 150 defining a lumen 152. With reference to FIG. 12, it will be appreciated that fixation tool shaft 146 includes a first prong 154A and a second prong 156B that extend distally beyond a distal end 158 of lumen 152. In the embodiment of FIG. 12A, first prong 154A and second prong 156B have been urged into tissue T to form first pilot hole 162A and second pilot hole 162B. In FIG. 12A a distally directed force F applied to fixation tool shaft 146 is illustrated using an arrow. Force F may be produced, for example, by pushing on a handle that is fixed to a proximal portion of fixation tool shaft 146. It will be appreciated that in some embodiments, such as the embodiment depicted in FIG. 6, one of the first and second pilot holes may be formed through the sheet-like implant and the target tissue, and the other pilot hole may be formed directly in the target tissue without passing through the sheet-like implant. In other words, in various embodiments staples may straddle the perimeter edge of the sheet-like implant (as shown in FIG. 6), may be applied adjacent to the perimeter, and/or be applied to a central region of the implant. In some embodiments, the staples may be used to attach the implant to soft tissue and/or to bone. In FIG. 12A, a staple 100 can be seen residing in lumen 152 of fixation tool shaft 146. For purposes of illustration, fixation tool shaft 146 is shown in partial cross-section in FIG. 12A so that staple 100 is visible residing in lumen 152. With reference to FIG. 12, it will be appreciated that staple 100 is carried by a fork 136 comprising a first stake 134A and a second stake 134B. In FIG. 12A, a distal portion of first stake 134A of staple push rod 130 can be seen extending through a first passageway defined by first fluke 106A. A distal portion of second stake 134B of staple push rod 130 can be seen extending through a second passageway defined by second fluke 106B of staple 100.

In some useful embodiments, each stake is positioned relative to a prong along an inner surface of fixation tool shaft 146 so that the stakes advance into the pilot holes when the stakes are moved in a distal direction. Staple push rod 130 is slidably disposed within lumen 152 defined by along fixation tool shaft 146. Fixation tool 144 includes a mechanism that is capable of creating relative axial motion between staple push rod 130 and fixation tool shaft 146 so that staple push rod 130 slides along fixation tool shaft 146.

At FIG. 12B, relative motion has been created between staple push rod 130 and fixation tool shaft 146 while distally directed force F has been continuously applied to fixation tool shaft 146. By comparing FIG. 12B and FIG. 12A, it will be appreciated that first stake 134A and second stake 134B have been advanced in a distal direction D. With reference to FIG. 12, it will also be appreciated that first stake 134A and second stake 134B have advanced into first pilot hole 162A and second pilot hole 162B, respectively. In FIG. 12B, first fluke 106A is shown residing in first pilot hole 162. Second fluke 106B is residing in second pilot hole 162 in the embodiment of FIG. 12B.

At FIG. 12C, additional relative motion has been created between staple push rod 130 and fixation tool shaft 146 while distally directed force F has been continuously applied to fixation tool shaft 146. By comparing FIG. 12C and FIG. 12B, it will be appreciated that the relative motion between staple push rod 130 and fixation tool shaft 146 has moved fixation tool shaft 146 in a proximal direction P.

By comparing FIG. 12C and FIG. 12B, it will also be appreciated that first arm 102A of staple 100 has been bent and first fluke 106A has been rotated to a toggled position. In the exemplary embodiment of FIG. 12C, force applied to first fluke 106A by first shoulder 142A has caused first fluke 106A to rotate. Also in the embodiment of FIG. 12C, the rotation of first fluke 106A has caused some bending in the distal portion 138 of first stake 134A. With continuing reference to FIG. 12C and FIG. 12B, it will be appreciated that second arm 102B of staple 100 has been bent and second fluke 106A has been rotated to a toggled position. In the exemplary embodiment of FIG. 12C, force applied to second fluke 106*b* by second shoulder 142B has caused second fluke 106B to rotate. Also in the embodiment of FIG. 12C, the rotation of second fluke 106B has caused some bending in the distal portion 138 of second stake 134B.

With reference to FIG. 12C, it will be appreciated that a first through hole 164A and a second through hole 164B have been formed in tendon repair implant 50. In the embodiment of FIG. 12, first through hole 164A and a second through hole 164B were created by urging first prong 154A and second prong 156B of fixation tool shaft 146 through tendon repair implant 50.

Figures 13A, 13B, 13C, 13D:
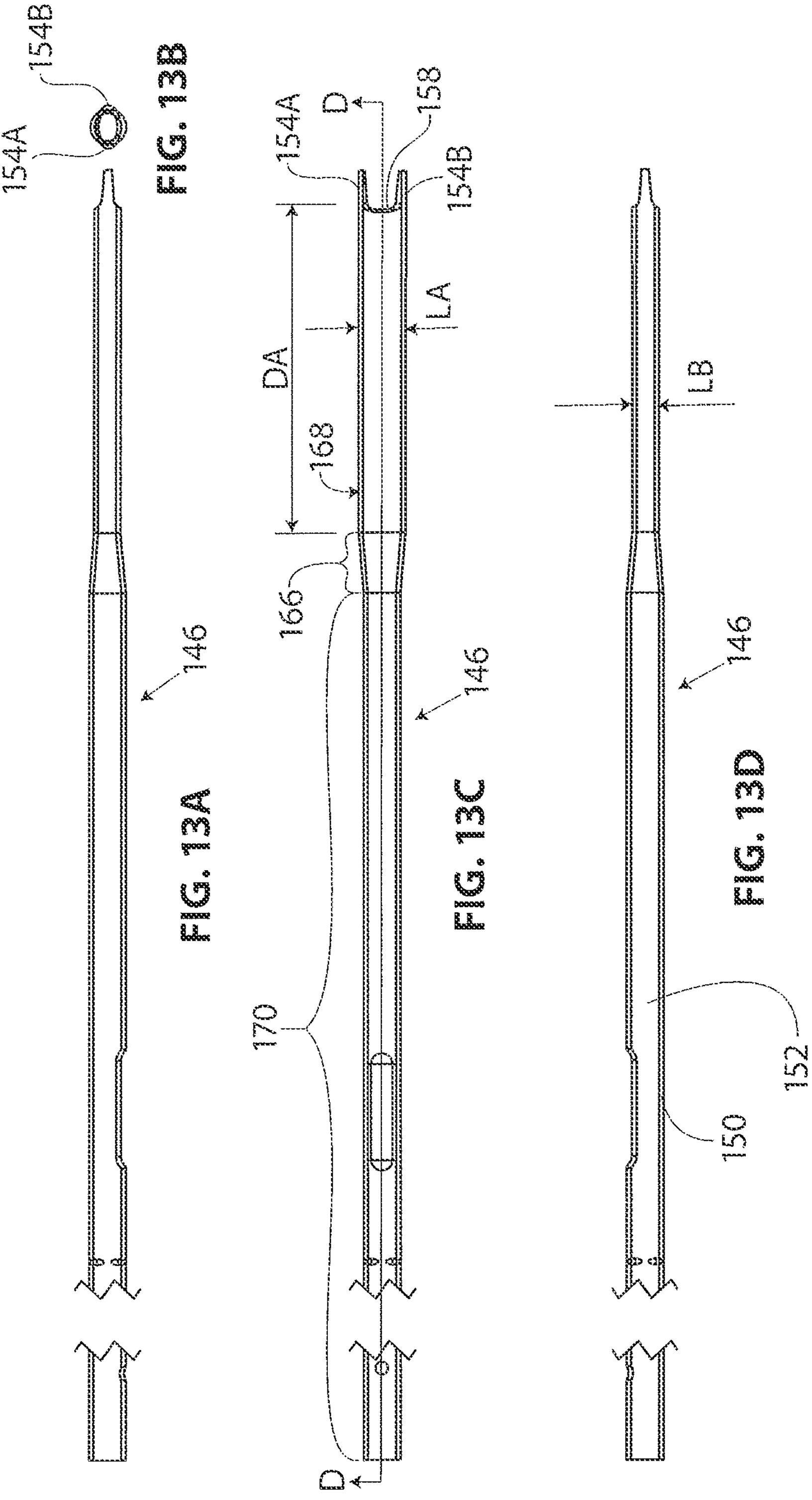
FIG. 13A, FIG. 13B, FIG. 13C and FIG. 13D are multiview projections illustrating a fixation tool shaft shown in the previous Figures.

FIG. 13A, FIG. 13B, and FIG. 13C are multiview projections illustrating a fixation tool shaft 146 shown in the previous Figures. FIG. 13D is a cross-sectional view of fixation tool shaft 146 sectioned along cutting plane D-D illustrated in FIG. 13C. These Figures may be collectively referred to as FIG. 13. Fixation tool shaft 146 of FIG. 13 comprises a wall 150 defining a lumen 152. A first prong 154A and a second prong 156B of fixation tool shaft 146 extend distally beyond a distal end 158 of lumen 152.

With reference to FIG. 13, it will be appreciated that fixation tool shaft 146 comprises a proximal portion 170, a distal portion 168 and an intermediate portion 166 disposed between proximal portion 170 and distal portion 168. In the embodiment of FIG. 13, distal portion 168 has an axial extent DA, a major lateral extent LA and a minor lateral extent LB. With reference to FIG. 13, it will be appreciated that axial extent DA is greater than both minor lateral extent LB and major lateral extent LA.

Figure 14:
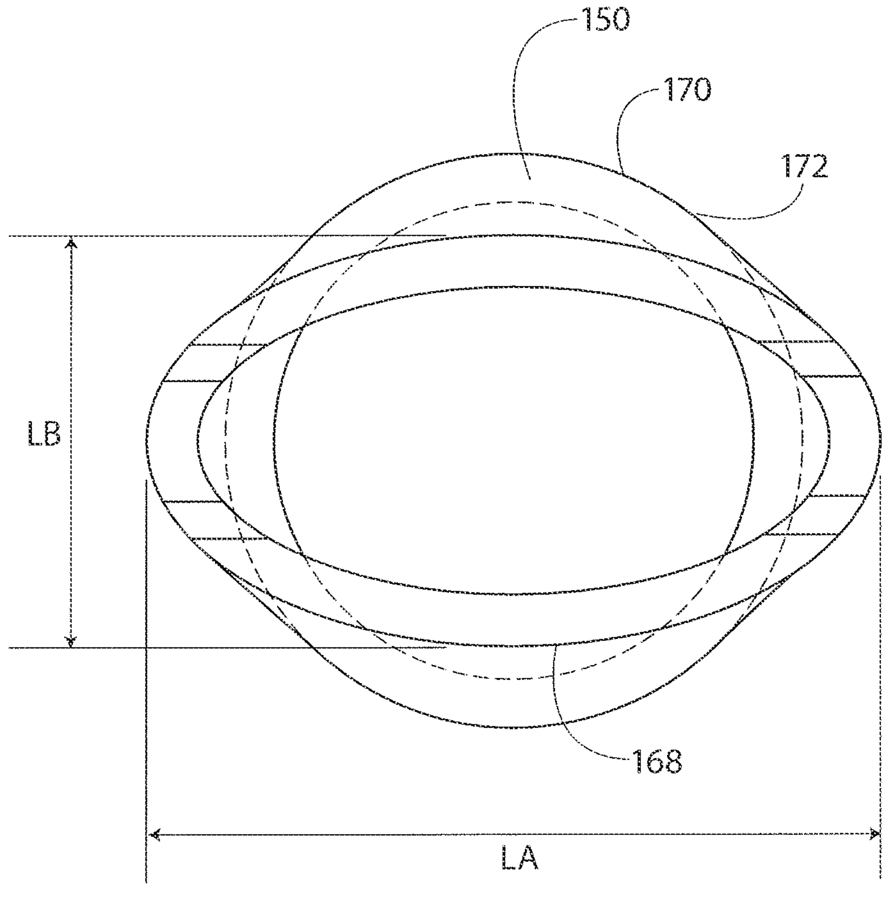
FIG. 14 is an enlarged axial view of the fixation tool shaft shown in the previous Figure.

FIG. 14 is an enlarged axial view of fixation tool shaft 146 shown in the previous Figure. With reference to FIG. 14, it will be appreciated that proximal portion 170 of fixation tool shaft 146 comprises a wall 150 having an outer surface 172. In FIG. 14, outer surface 172 is illustrated using a circle. Thus, it will be appreciated that proximal portion 170 of fixation tool shaft 146 has a generally cylindrical outer shape in the exemplary embodiment of FIG. 14. In the exemplary embodiment of FIG. 14, fixation tool shaft 146 has a generally uniform wall thickness. Accordingly, the shape of proximal portion 170 may be generally described as a cylindrical tube. The shape of distal portion 168 may be described as a cylindrical-tube that has been partially flattened. In the exemplary embodiment of FIG. 14, distal portion 168 of fixation tool shaft 146 has a major lateral extent LA and a minor lateral extent LB. With reference to FIG. 14, it will be appreciated that major lateral extent LA is greater than minor lateral extent LB.

Figure 15:
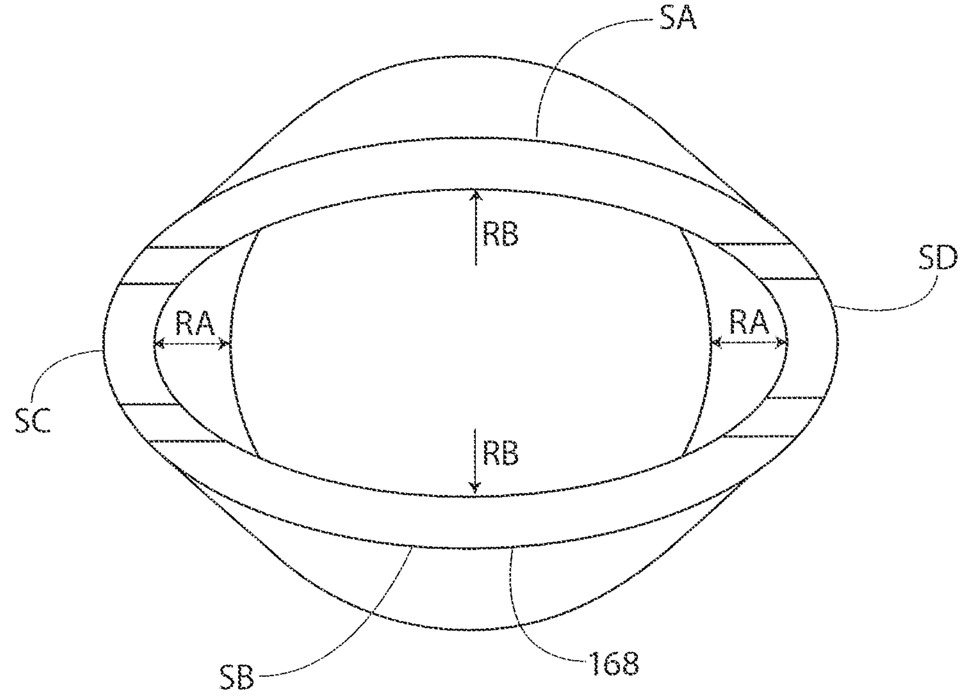
FIG. 15 is an additional enlarged axial view of the fixation tool shaft shown in the previous Figure.
Figure 15:
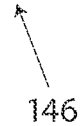

FIG. 15 is an additional enlarged axial view of fixation tool shaft 146. With reference to FIG. 15, it will be appreciated that distal portion 168 of fixation tool shaft 146 comprises a first major side SA, a second major side SB, a first minor side SC, and a second minor side SD. In the exemplary embodiment of FIG. 15, each minor side has a first central radius RA and each major side has a second central radius RB. With reference to FIG. 15, it will be appreciated that second central radius RB is greater than first central radius RA. In the exemplary embodiment of FIG. 15, first major side SA, second major side SB, first minor side SC, and second minor side SD each have a generally convex shape. In the exemplary embodiment of FIG. 15, each minor side is generally more convex than each major side.

Figure 16:
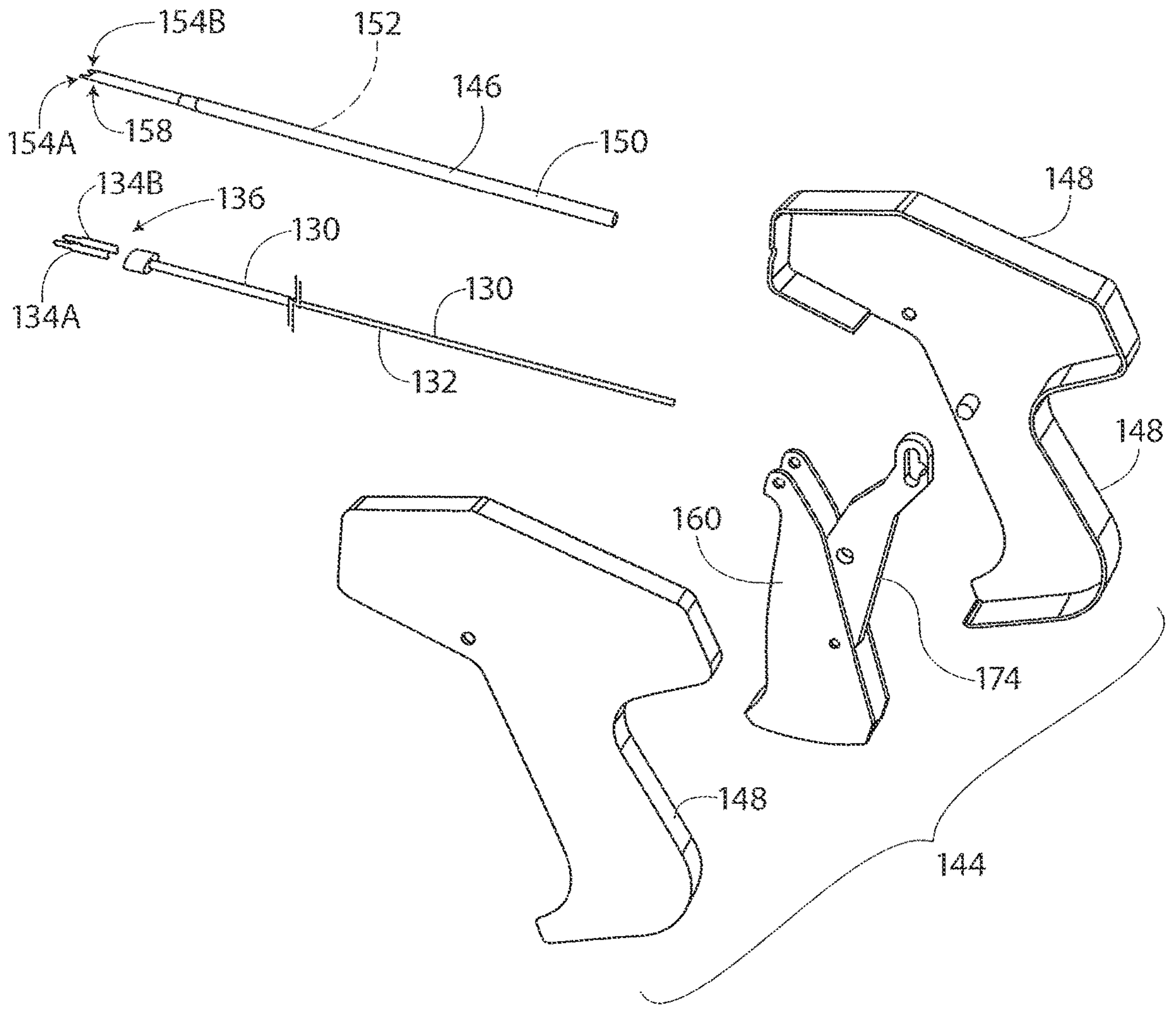
FIG. 16 is an exploded isometric view of an exemplary fixation tool in accordance with this detailed description.

FIG. 16 is an exploded isometric view of an exemplary fixation tool 144 in accordance with this detailed description. In the embodiment of FIG. 16, fixation tool 144 comprises a fixation tool shaft 146 and a handle 148. In FIG. 16, handle 148 is exploded into two pieces. A proximal portion of fixation tool shaft 146 is fixed to handle 148 when fixation tool 144 is in an assembled state. Fixation tool shaft 146 comprises a wall 150 defining a lumen 152.

When fixation tool 144 is in an assembled state a staple push rod 130 extends into lumen 152 of fixation tool shaft 146. Staple push rod 130 comprises a fork 136 and a shaft 132. Fork 136 comprises a first stake 134A and a second stake 134B. Shaft 132 is coupled between fork 136 and a lever 174. Lever 174 is coupled to a trigger 160. Trigger 160 is pivotably coupled to handle 148 of fixation tool 144 when fixation tool 144 is in an assembled state. In operation, staple push rod 130 will be advanced and/or retracted in an axial direction when trigger 160 is pivoted relative to handle 148.

While exemplary embodiments of the present invention have been shown and described, modifications may be made, and it is therefore intended in the appended claims and subsequently filed claims to cover all such changes and modifications which fall within the true spirit and scope of the invention.

What is claimed is:

1. A fixation device for attaching a sheet-like implant to a target tissue, comprising:

a handle assembly including a trigger;

an elongate tube extending distally from the handle assembly, a distal end of the elongate tube including a pair of distally extending pilot-hole forming prongs;

a staple disposed within the elongate tube and axially deployable from a distal end of the elongate tube, the staple including a first fluke, a second fluke, and a bridge connecting the first fluke and the second fluke;

a first stake configured to releasably engage the first fluke of the staple and extend proximally therefrom;

a second stake configured to releasably engage the second fluke of the staple and extend proximally therefrom;

wherein actuation of the trigger causes the staple to move distally relative to the elongate tube to deploy the staple from the distal end of the elongate tube;

wherein the first and second flukes are positioned relative to the pair of distally extending pilot-hole forming prongs so that the first and second flukes advance distally into pilot-holes formed by the pair of distally extending pilot-hole forming prongs as the staple is deployed from the distal end of the elongate tube.

2. The fixation device of claim 1, wherein the pair of stakes are configured and adapted to impart a distally directed force on the staple such that the staple moves distally relative to the elongate tube distally beyond the pair of distally extending pilot-hole forming prongs.

3. The fixation device of claim 1, wherein the first fluke includes a first passage extending at least partially through the first fluke and the second fluke includes a second passage extending at least partially through the second fluke.

4. The fixation device of claim 3, wherein the first stake extends into the first passage and the second stake extends into the second passage.

5. The fixation device of claim 1, wherein the first fluke includes a first passage extending entirely through the first fluke from a proximal opening to a distal opening, and the second fluke includes a second passage extending entirely through the first fluke from a proximal opening to a distal opening.

6. The fixation device of claim 5, wherein the first stake extends entirely through the first passage and distally of the distal opening of the first passage, and the second stake extends entirely through the second passage and distally of the distal opening of the second passage.

7. The fixation device of claim 1, wherein the first stake includes a shoulder configured to engage a proximal surface of the first fluke and the second stake includes a should configured to engage a proximal surface of the second fluke.

8. The fixation device of claim 1, wherein the first and second stakes are secured to and extend distally from a push rod.

9. The fixation device of claim 8, wherein the push rod is slidably disposed in the elongate tube.

10. The fixation device of claim 1, wherein a distal end region of the elongate tube has a major lateral extent and a minor lateral extent perpendicular to the major lateral extent, wherein the major lateral extent is greater than the minor lateral extent.

11. The fixation device of claim 10, wherein the distal end region of the elongate tube has an oval cross-section.

12. A fixation device for attaching a sheet-like implant to a target tissue, comprising:

a tubular shaft having a proximal end, a distal end, and first and second prongs extending distally therefrom, the first and second prongs configured to form pilot-holes when pressed against the target tissue;

a staple disposed within a lumen of the tubular shaft, the staple comprising a first arm, a second arm, and a bridge connecting the first arm and the second arm; and a staple push rod longitudinally moveable within the lumen of the tubular shaft, the staple push rod configured to impart a distally directed force to the staple disposed within the tubular shaft such that the staple moves distally relative to the tubular shaft distally beyond the first and second prongs;

wherein the staple push rod is configured to advance the first and second arms of the staple distally into pilot-holes formed by the pair of distally extending pilot-hole forming prongs; and wherein the first and second arms of the staple splay outward in opposite directions when expelled distally beyond the first and second prongs.

13. The fixation device of claim 12, wherein the staple push rod includes first and second stakes engaged with the first and second arms of the staple.

14. The fixation device of claim 13, wherein the staple push rod is longitudinally moveable between a retracted position in which distal ends of the first and second stakes are positioned within the lumen of the tubular shaft and an extended position in which the distal ends of the first and second stakes are positioned distal of the first and second prongs.

15. The fixation device of claim 14, wherein a portion of the staple is positioned between laterally outward surfaces of the first and second stakes and an interior surface of the tubular shaft in the retracted position.

16. The fixation device of claim 14, wherein the first and second stakes splay outward in opposite directions when moved to the extended position.

17. The fixation device of claim 13, wherein the first stake is disposed within a passage of the first arm of the staple and the second stake is disposed within a passage of the second arm of the staple.

18. The fixation device of claim 17, wherein each of the first and second arms of the staple comprises a trunk portion and a fluke portion, wherein the fluke portion is offset from the trunk portion, and wherein the passage extends at least partially through the fluke portion of each arm.

19. The fixation device of claim 18, wherein the trunk portions are configured to bend under reaction forces when placed in tissue causing the fluke portions to rotate in opposite directions.

* * * * *